United States Patent
Mao et al.

(10) Patent No.: US 12,312,304 B2
(45) Date of Patent: May 27, 2025

(54) METHOD FOR CONTINUOUS SYNTHESIS OF ACYLNAPHTHALENE WITH ACYLATION LIQUID

(71) Applicant: CCTEG CHINA COAL RESEARCH INSTITUTE, Beijing (CN)

(72) Inventors: Xuefeng Mao, Beijing (CN); Heng Li, Beijing (CN); Fating Hu, Beijing (CN); Jinlong Zhong, Beijing (CN); Junfang Li, Beijing (CN); Tong Wang, Beijing (CN); Xiaoran Zhang, Beijing (CN)

(73) Assignee: CCTEG CHINA COAL RESEARCH INSTITUTE, Beijing (CN)

( * ) Notice: Subject to any disclaimer, the term of this patent is extended or adjusted under 35 U.S.C. 154(b) by 375 days.

(21) Appl. No.: 18/057,394

(22) Filed: Nov. 21, 2022

(65) Prior Publication Data

US 2023/0095165 A1 Mar. 30, 2023

Related U.S. Application Data

(63) Continuation of application No. PCT/CN2022/115478, filed on Aug. 29, 2022.

(30) Foreign Application Priority Data

| Sep. 14, 2021 | (CN) | 202111075055.5 |
| Sep. 17, 2021 | (CN) | 202111093577.8 |
| Dec. 29, 2021 | (CN) | 202111638857.2 |
| Jan. 26, 2022 | (CN) | 202210095938.0 |
| Feb. 14, 2022 | (CN) | 202210135569.3 |
| May 16, 2022 | (CN) | 202210530956.7 |

(51) Int. Cl.
C07C 45/46 (2006.01)
C07C 45/84 (2006.01)

(52) U.S. Cl.
CPC ............ C07C 45/46 (2013.01); C07C 45/84 (2013.01)

(58) Field of Classification Search
CPC .................. C07C 45/46; C07C 45/84
See application file for complete search history.

(56) References Cited

FOREIGN PATENT DOCUMENTS

| CN | 1209348 | | 3/1999 |
| CN | 1817843 | A | 8/2006 |
| CN | 101177377 | | 5/2008 |
| CN | 101774879 | A | 7/2010 |
| CN | 102786445 | | 11/2012 |
| CN | 104225946 | A | 12/2014 |
| CN | 104261590 | A | 1/2015 |
| CN | 206661208 | U | 11/2017 |
| CN | 107879909 | A | 4/2018 |
| CN | 108003007 | A | 5/2018 |
| CN | 108640330 | | 10/2018 |
| CN | 108745252 | A | 11/2018 |
| CN | 110105191 | | 8/2019 |
| CN | 211462268 | U | 9/2020 |
| CN | 112321429 | A | 2/2021 |
| CN | 113773179 | | 12/2021 |
| CS | 274233 | | 4/1991 |
| JP | H08281002 | | 10/1996 |

OTHER PUBLICATIONS

CNIPA, First Office Action for CN Application No. 202210530956.7, Dec. 29, 2022.
CNIPA, First Office Action for CN Application No. 202111638857.2, Jul. 20, 2023.
CNIPA, First Office Action for CN Application No. 202210095938.0, Aug. 11, 2023.
CNIPA, First Office Action for CN Application No. 202210135569.3, Aug. 22, 2023.
Teng et al., "Essence of β-methylnaphthalene make," Journal of Jiamusi University (Natural Science Edition), 2004, vol. 22, No. 4.
CNIPA, Office Action for CN Application No. 202111075055.5, Sep. 20, 2022.
WIPO, International Search Report for International Application No. PCT/CN2022/115478, Nov. 28, 2022.
Li, Wenpeng, Study on the preparation of 2-methyl-6-acylnaphthalene by acylation of 2-methylnaphthalene in a microchannel, China Excellent Master's Degree Thesis Library, Engineering Science and Technology 1, Jan. 15, 2019, B016-120, Issue 01.

*Primary Examiner* — Sikarl A Witherspoon
(74) *Attorney, Agent, or Firm* — Hodgson Russ LLP

(57) ABSTRACT

A method for continuous synthesis of acylnaphthalene includes: mixing a raw solution containing 2-methylnaphthalene with an acylation liquid to obtain an acylation reaction liquid with a molar ratio of the 2-methylnaphthalene: the acylation agent: the Lewis catalyst of 1:1.3:1.5; adding the acylation reaction liquid into a microchannel reactor and a plurality of kettle reactors connected in series to perform acylation reaction, performing hydrolysis reaction on the acylation reaction liquid immediately after the acylation reaction liquid flows out of the plurality of kettle reactors to obtain a mixed solution, and subjecting the mixed solution to separation, rectification and crystallization, to obtain 2-methyl-6-propionylnaphthalene.

20 Claims, 7 Drawing Sheets

METHOD FOR CONTINUOUS SYNTHESIS OF ACYLNAPHTHALENE WITH ACYLATION LIQUID

CROSS-REFERENCE TO RELATED APPLICATIONS

The present disclosure is a continuation of International Patent Application No. PCT/CN2022/115478 filed on Aug. 29, 2022, which claims priority to the following applications:
Chinese Patent Application Serial No. 202111075055.5, filed on Sep. 14, 2021;
Chinese Patent Application Serial No. 202111093577.8, filed on Sep. 17, 2021;
Chinese Patent Application Serial No. 202111638857.2, filed on Dec. 29, 2021;
Chinese Patent Application Serial No. 202210095938.0, filed on Jan. 26, 2022;
Chinese Patent Application Serial No. 202210135569.3, filed on Feb. 14, 2022; and
Chinese Patent Application Serial No. 202210530956.7, filed on May 16, 2022.
The entire disclosures of the above-mentioned applications are incorporated herein by reference.

FIELD

The present disclosure relates to a chemical synthesis technical field, and more particularly to an acylation liquid and a method for continuous synthesis of acylnaphthalene with an acylation liquid.

BACKGROUND

In the related art, acylnaphthalene such as 2-methyl-6-propionylnaphthalene is prepared through a Friedel-Crafts acylation reaction at room temperature under an atmospheric pressure. However, problems, such as unstable acylation liquid, poor homogeneity, low reaction efficiency, unstable hydrolysis process, blockage of pipelines, and low purity and yield of the acylnaphthalene, still exist in the art.

Therefore, there is a need for improving the synthesis of the acylnaphthalene.

SUMMARY

The present disclosure seeks to solve at least one of the problems existing in the related art to at least some extent.

Accordingly, a method for continuous synthesis of acylnaphthalene is provided. The method includes: mixing a raw solution containing 2-methylnaphthalene with an acylation liquid to obtain an acylation reaction liquid with a molar ratio of the 2-methylnaphthalene: the acylation agent: the Lewis catalyst of 1:1.3:1.5; adding the acylation reaction liquid into a microchannel reactor and a plurality of kettle reactors connected in series to perform acylation reaction; and performing hydrolysis reaction on the acylation reaction liquid immediately after the acylation reaction liquid flows out of the plurality of kettle reactors to obtain a mixed solution, and subjecting the mixed solution to separation, rectification and crystallization, to obtain 2-methyl-6-propionylnaphthalene.

In some embodiments, the raw solution and the acylation liquid are injected into a three-way mixer through a syringe for mixing.

In some embodiments, the three-way mixer and the microchannel reactor are placed in a first thermostatic bath at a temperature of −5° C. to 0° C., and the kettle reactor is placed in a second thermostatic bath at a temperature of 30° C. to 50° C.

In some embodiments, two to four kettle reactors are provided and connected in series with each other, and a total residence time of the acylation reaction liquid in the kettle reactor is in a range of 50 to 80 min.

In some embodiments, performing the hydrolysis reaction includes: introducing water into a water phase pipeline of a hydrolysis section before introducing the acylation reaction liquid obtained after the acylation reaction into the hydrolysis section; introducing the acylation reaction liquid into an oil phase pipeline of the hydrolysis section after the water flows out of an outlet of the hydrolysis section; mixing the acylation reaction liquid with the water in a low temperature cold bath to obtain a mixed solution, and introducing the mixed solution into a tubular reactor for the hydrolysis reaction; discharging the mixed solution after the hydrolysis reaction through an outlet of the tubular reactor. During the hydrolysis reaction, the water is kept in a preset flowing state until the mixed solution is completely discharged.

In some embodiments, subjecting the mixed solution to the separation includes: collecting the mixed solution and separating a water phase and an oil phase of the mixed solution by using a liquid separator.

In some embodiments, the water is introduced into the water phase pipeline of the hydrolysis section at a flow rate of 3 to 15 mL/min through a water injection pump. A temperature of the low temperature cold bath is in a range of 0° C. to 20° C. A reaction temperature of the tubular reactor is a range of 30° C. to 40° C.

In some embodiments, the present method further includes: performing acylation wastewater treatment. The acylation wastewater treatment includes: adjusting a pH value of the water phase separated by the liquid separator to alkalinity to obtain a suspension containing an aluminum hydroxide precipitate, and filtering the suspension to obtain an aluminum hydroxide filter cake and a filtrate; adjusting a pH value of the filtrate to acidity, and adding an extractant to the filtrate, to obtain a raffinate phase and an extraction phase after stirring and standing; discharging the raffinate phase after being subjected to biochemical treatment; rectifying and separating the extraction phase to obtain nitrobenzene and the extractant. The nitrobenzene is reused as an organic solvent, and the extractant is reused for the extraction of the filtrate; dissolving the filter cake with concentrated hydrochloric acid by heating to obtain a solution, and adding an additive into the solution for polymerization to obtain polyaluminum chloride.

In some embodiments, adjusting the pH value of the water phase separated by the liquid separator to alkalinity includes: adjusting the pH value of the water phase to a range of 8 to 10 with an alkali, and the alkali is selected from sodium hydroxide, potassium hydroxide, liquid ammonia or a combination thereof.

In some embodiments, adjusting the pH value of the filtrate to acidity includes: adjusting the pH value of the filtrate to a range of 2 to 3 with an acid. The acid is selected from hydrochloric acid, nitric acid, sulfuric acid or a combination thereof.

In some embodiments, the extractant is a non-polar organic solvent, and a volume ratio of the extractant to the filtrate is 0.5:1 to 5:1, and the extractant is selected from n-heptane, n-octane, n-hexane, benzene, toluene, xylene, carbon tetrachloride or a combination thereof.

In some embodiments, a temperature for dissolving the filter cake is in a range of 40° C. to 50° C., and a weight ratio of the filter cake to concentrated hydrochloric acid is 0.5:1 to 2.5:1.

In some embodiments, an amount of the additive is in a range of 2 to 10 wt % based on a dry weight of the filter cake, and the additive is selected from calcium aluminate, magnesium aluminate or a combination thereof.

In some embodiments, the rectifying includes: feeding the oil phase into a first rectification column from a middle of the first rectification column for distillation, discharging a first light fraction from a top of the first rectification column and recycling the first light fraction after condensation, and discharging a bottom liquid from a bottom of the first rectification column; pumping the bottom liquid still hot to a second rectification column for further distillation, discharging a second light fraction from a top of the second rectification column and collecting the second light fraction after condensation, and collecting a product from a side stream of the second rectification column; heating a heavy bottom fraction from the second rectification column with a reboiler, and pumping the heavy bottom fraction still hot to a bottom collection tank.

In some embodiments, the first rectification column has a pressure in a range of 0.05 KPa to 10 KPa and a reflux ratio in a range of 1:1 to 2:1. A condensation temperature of the first rectification column is in a range of 10° C. to 20° C.

In some embodiments, the second rectification column has a pressure in a range of 0.05 KPa to 10 KP and a reflux ratio in a range of 5:1 to 10:1. A condensation temperature of the second rectification column is in a range of 50° C. to 90° C.

In some embodiments, the 2-methylnaphthalene has a purity of 99.0 to 99.9%, and is extracted from a wash oil by: performing distillation and separation on the wash oil to obtain a methylnaphthalene-enriched fraction; introducing the methylnaphthalene-enriched fraction into an azeotropic rectification column for azeotropic distillation to obtain an azeotropic distillate; introducing the azeotropic distillate into a separator to obtain crude 2-methylnaphthalene; introducing the crude 2-methylnaphthalene into a plurality of batch melting crystallizers arranged in parallel for crystallization and purification to obtain the 2-methylnaphthalene.

In some embodiments, the acylation liquid is prepared by: weighing a Lewis catalyst under inert gas protection; adding a solvent and the Lewis catalyst into a first chamber through a first feeding port and mixing them with an agitator to obtain a mixture solution; and adding an acylation agent into the mixture solution with a feeding pump to obtain the acylation liquid. A molar mass ratio of the acylation agent to the Lewis catalyst is (1.1 to 1.5):(1.3 to 1.7); and/or a molar mass ratio of the Lewis catalyst to the solvent is 1.3:5 to 1.7:5.

In some embodiments, the solvent is nitrobenzene, and adding the nitrobenzene and the Lewis catalyst into the first chamber and mixing them includes: adding the nitrobenzene into the first chamber through the first feeding port; adding the Lewis catalyst to the nitrobenzene in the first chamber; and heating the nitrobenzene and the Lewis catalyst to 50° C. to 60° C. by using the heat exchange medium under stirring at a stirring speed of 200 rpm to 400 rpm with the agitator.

In some embodiments, preparing the acylation liquid further includes: filtering the acylation liquid in an inert gas atmosphere with a suction filtering device to obtain a filtered acylation liquid.

In some embodiments, the acylation agent is added at a speed of 3 drops to 10 drops per second, and a stirring speed of the agitator is 200 rpm to 400 rpm.

BRIEF DESCRIPTION OF THE DRAWINGS

These and/or other aspects and advantages of embodiments of the present disclosure will become apparent and more readily appreciated from the following descriptions made with reference to the drawings, in which.

REFERENCE NUMERALS

Figure 1:
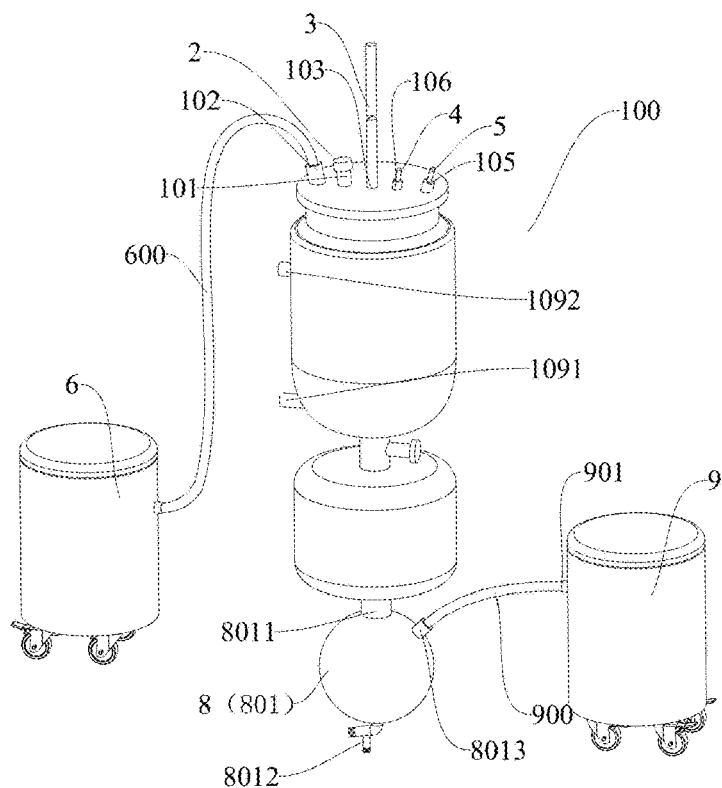
FIG. 1 is a schematic diagram showing a preparation system according to some embodiments of the present disclosure.

100: preparation system;
1: kettle body; 101: first feeding port; 102: second feeding port; 103: stirring port; 104: liquid outlet; 1041: first control valve; 105: temperature measuring port; 106: pH meter port; 107: first shell; 108: upper cover; 109: Jacket; 1091: first inlet for heat exchange medium; 1092: first outlet for heat exchange medium; 110: first chamber;
2: feeding port cover;
3: agitator; 301: stirring shaft; 302: stirring blade;
4: pH meter;
5: temperature sensor;
6: feeding pump; 600: first pipe;
7: filtering device; 701: second shell; 7011: filtering device inlet; 7012: filtering device outlet; 7013: first part; 7014: second part; 702: filtering membrane;

8: liquid reservoir; 801: third shell; 8011: liquid reservoir inlet; 8012: liquid reservoir outlet; 8013: second vacuum pumping port;
9: vacuum pump; 900: second pipe; 901: first vacuum pumping port;
10: glass cover; 1001: fitting surface;
11: three-way mixer;
12: microchannel reactor;
13: kettle reactor;
14: raw solution;
15: acylation liquid;
16: liquid separator; 1601: exhaust outlet; 1602: feeding inlet; 1603: control valve; 1604: container; 1605: discharging outlet;
1701: regulation tank; 1702: sedimentation tank; 1703: filtering unit; 1704: extraction unit; 1705: rectification column; 1706: biochemical treatment unit; 17061: aeration tank; 17602: secondary sedimentation tank; 1707: dissolution tank; 1708: reaction kettle;
1801: wash oil; 1802: naphthalene light oil fraction; 1803: methylnaphthalene-enriched fraction; 1804: heavy oil fraction; 1805: azeotropic distillate; 1806: residual oil; 1807: azeotropic agent mixture; 1808: crude methylnaphthalene; 1809: water; 1810: azeotropic agent; 1811: heating and cooling medium; 1812: residual mother liquor; 1813: methylnaphthalene product; 1814: first temperature control medium outlet; 1815: first temperature control medium inlet; 1816: material inlet; 1817: material outlet; 1818: second temperature control medium inlet; 1819: second temperature control medium outlet; 1820: protrusion; 1821: groove; 1822: spiral groove;
V1: wash oil tank; V2: atmospheric rectification column; V3: azeotropic rectification column; V4: ultrasonic static mixer; V5: separator; V6: rectification column; V7: digital temperature-controlled oil bath; V8: batch melting crystallizer.

DETAILED DESCRIPTION

In order to make the objects, technical solutions and advantages of the present disclosure clear, embodiments of the present disclosure will be further described below in combination with accompanying drawings. It should be noted that embodiments of the present disclosure and the features in embodiments may be combined with each other when they are not in conflict to each other.

The present disclosure is described in details in the following description to facilitate the understanding of the present disclosure. However, the present disclosure may also be implemented in other ways different from those described here. Therefore, the scope claimed by the present disclosure shall be subject to the appended claims.

Figure 2:
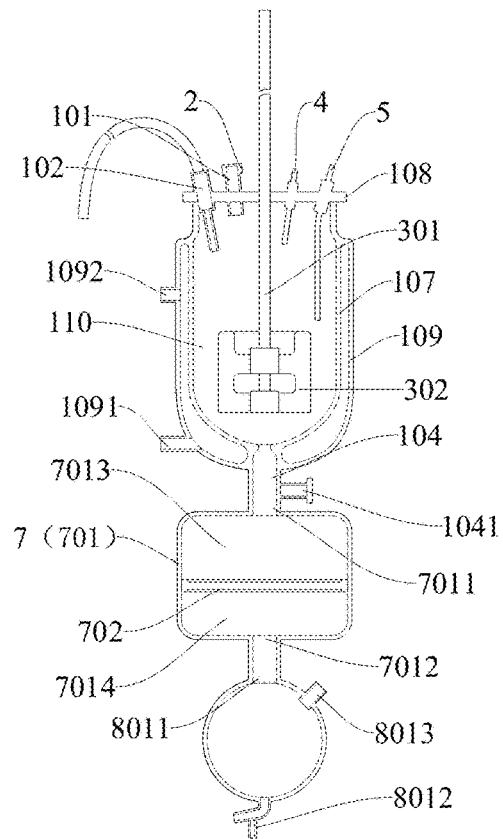
FIG. 2 is a schematic diagram showing a kettle body, a filtering device and a liquid reservoir of the preparation system in FIG. 1.
Figure 3:
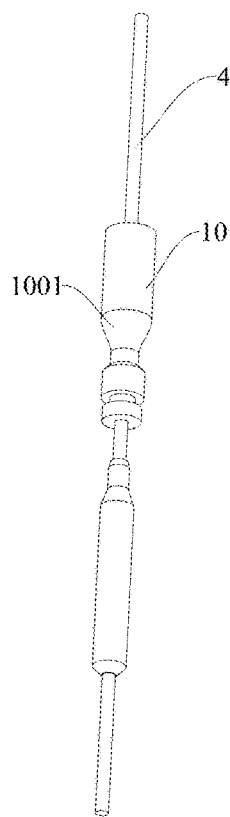
FIG. 3 is a schematic diagram showing a pH meter in FIG. 2.

As shown in FIG. 1 to FIG. 3, a preparation system 100 for preparing an acylation liquid in embodiments of the present disclosure includes a kettle body 1, a feeding port cover 2, a feeding pump 6 and an agitator 3. The kettle body 1 defines a first chamber 110, and has a first feeding port 101, a second feeding port 102, a stirring port 103 and a liquid outlet 104 that are communicated with the first chamber 110.

In some embodiments, each of the first feeding port 101, the second feeding port 102 and the stirring port 103 is located above the liquid outlet 104.

In this way, a solvent and Lewis catalyst for preparing the acylation liquid may be added into the first chamber 110 through the first feeding port 101, and an acylation agent may be added into the first chamber 110 through the second feeding port 102.

The feeding port cover 2 is detachably attached on and hermetically sealed with the first feeding port 101. When raw materials (the solvent and the Lewis catalyst) are fed into the kettle body 1, the feeding port cover 2 is removed from the first feeding port 101. After the feeding is completed, the feeding port cover 2 is hermetically covered on the first feeding port 101 immediately, which reduces the contact time between the solvent/the Lewis catalyst and external environment, and reduces the exposure time of the first chamber 110 to the external environment through the first feeding port 101.

The feeding pump 6 is hermetically connected with the second feeding port 102, such that the acylation agent is added through the second feeding port 102. In this way, during and after feeding to the first chamber 110 by using the feeding pump 6, the contact between the acylation agent and the external environment may be effectively avoided, and the first chamber 110 may be prevented from being exposed to the external environment through the second feeding port 102.

Part of the agitator 3 is hermetically inserted in the stirring port 103, and the agitator 3 includes a stirring shaft 301 and a plurality of stirring blades 302 disposed on the stirring shaft 301. At least a part of the stirring shaft 301 and each of the stirring blades 302 are located in the first chamber 110.

In this way, the agitator 3 may fully stir and mix the materials in the first chamber 110 to fully dissolve the Lewis catalyst and improve preparation efficiency of the acylation liquid. In addition, the part of the agitator 3 is hermetically inserted in the stirring port 103, such that the stirring port 103 is always sealed during the operation of the agitator 3, which prevents the first chamber 110 from being exposed to the external environment through the stirring port 103.

In some embodiments of the present disclosure, preparing the acylation liquid with the preparation system 100 includes a) weighing a Lewis catalyst under inert gas protection; b) adding a solvent and the Lewis catalyst weighed in step a) into the first chamber 110 through the first feeding port 101 and evenly stirring them with the agitator 3 to obtain a mixture solution; and c) adding, by the feeding pump 6, an acylation agent into the mixture solution obtained in step b), and stirring them with the agitator 3 to obtain the acylation liquid.

In the method for preparing the acylation liquid in the embodiments of the present disclosure, the Lewis catalyst is weighed under the inert gas protection, which effectively ensures the activity of the Lewis catalyst, and avoids formation of acid mist due to a weather environment with high humidity for example in summer. In the method for preparing the acylation liquid in embodiments of the present disclosure, after the Lewis catalyst is weighed in the inert environment, it is added to the solvent, and the feeding port cover 2 is covered, which reduces the contact time between the Lewis catalyst and the air by liquid sealing. In this way, during preparing the acylation liquid, the contact between the Lewis catalyst/the acylation agent and water may be effectively reduced, and the stability and homogeneity of the prepared acylation liquid are improved. In the method for preparing the acylation liquid in the embodiments of the present disclosure, the Lewis catalyst may be fully and rapidly dissolved in the solvent under stirring of the agitator 3, which reduces the preparation time of the acylation liquid and improves the preparation efficiency of the acylation liquid. The acylation liquid prepared by the method for preparing the acylation liquid in the embodiments of the present disclosure has good homogeneity and high stability, and may be used in a microchannel reactor and improve the reaction efficiency therein.

In some embodiments, in step a), the Lewis catalyst is selected from at least one of $AlCl_3$, $BF_3$, $ZnCl_2$ or $FeCl_3$. In some embodiments, the Lewis catalyst may be selected according to actual needs, and the Lewis catalyst used to prepare 2-methyl-6-propionylnaphthalene can be used to prepare the acylation liquid by using the method for preparing the acylation liquid according to the embodiments of the present disclosure. The acylation agent may be selected from at least one of a group consisting of an acetylation agent, a propionylation agent, or a butyrylation agent.

In some embodiments, the feeding pump 6 is a peristaltic pump.

In some embodiments, the second feeding port 102 is a grinding port. The second feeding port 102 is hermetically communicated with a pagoda joint, and a discharging pipe of the peristaltic pump is hermetically communicated with the pagoda joint.

In this way, a flow rate of the peristaltic pump may be adjusted to control a flow rate of the acylation agent added into the first chamber 110 of the kettle body 1, such that an amount of the acylation agent added into the first chamber 110 may be conveniently controlled to further improve the stability and the homogeneity of the prepared acylation liquid.

In some embodiments, the feeding pump 6 is communicated with the second feeding port 102 through a first pipe 600. The first pipe 600 may be a polytetrafluoroethylene pipe.

In some embodiments, each of the stirring shaft 301 and the stirring blade 302 is formed of a metal material. The agitator 3 includes an anti-corrosion shaft layer and an anti-corrosion blade layer. The anti-corrosion shaft layer is coated on a part of the stirring shaft 301, and the anti-corrosion blade layer is coated on the stirring blades 302.

In some embodiments, each of the stirring shaft 301 and the stirring blade 302 is formed of a stainless steel material, and each of the shaft anti-corrosion layer and the blade anti-corrosion layer is formed of a polytetrafluoroethylene material.

Each of the stirring shaft 301 and the stirring blade 302 is made of the metal, which may improve structural strength of each of the stirring shaft 301 and the stirring blade 302. By coating the anti-corrosion shaft layer on the stirring shaft 301 and the anti-corrosion blade layer on the stirring blades 302, the metal material parts of the stirring shaft 301 and the stirring blades 302 may be prevented from contacting the solvent, the Lewis catalyst and the acylation agent, which avoids the corrosion of the stirring shaft 301 and the stirring blade 302, and prevents corrosion products from entering the acylation liquid and affecting the quality of the prepared acylation liquid.

In some embodiments, in step c), the acylation agent is added at a speed of 3 drops to 10 drops per second, and a stirring speed of the agitator is in a range of 200 rpm to 400 rpm.

In some embodiments, as shown in FIG. 2, the kettle body 1 includes a first shell 107, an upper cover 108 and a jacket 109. The liquid outlet 104 is located on the first shell 107, and the first shell 107 has an opening at its upper end. The upper cover 108 is hermetically covered on the opening of the first shell 107. The first shell 107 and the upper cover 108 define the first chamber 110, and each of the first feeding port 101, the second feeding port 102 and the mixing port 103 is located at the upper cover 108. The jacket 109 is fitted over the first shell 107. The jacket 109 has a first inlet 1091 for a heat exchange medium for feeding the heat exchange medium and a first outlet 1092 for the heat exchange medium for discharging the heat exchange medium.

In this way, during manufacturing the kettle body 1, the first shell 107 and the upper cover 108 may be manufactured separately to facilitate the manufacture of the kettle body 1. During the dissolution of the Lewis catalyst, the heat exchange medium may be fed into the jacket 109 through the first inlet 1091 to exchange heat with the materials in the first chamber 110 through the first shell 107, and then the heat exchange medium may be discharged from the jacket 109 through the first outlet 1092, thereby heating the material in the first chamber 110. In this way, a temperature in the first chamber 110 may be kept at a preset temperature suitable for the Lewis catalyst and the solvent, and the Lewis catalyst may be quickly dissolved in the solvent, thereby greatly reducing the preparation time of the acylation liquid and improving the preparation efficiency of the acylation liquid.

The heat exchange medium may be water, oil and other liquids.

In some embodiments, the solvent is nitrobenzene, and the step b) includes: adding the nitrobenzene into the first chamber 110 through the first feeding port 101; adding the Lewis catalyst weighed in step a) to the nitrobenzene in the first chamber 110; and heating the nitrobenzene and the Lewis catalyst to a temperature of 50° C. to 60° C. with the heat exchange medium in the jacket 109 under stirring at a stirring speed of 200 rpm to 400 rpm with the agitator 3, so as to dissolve the Lewis catalyst weighed in step a) to obtain the mixture solution.

In this way, the temperature in the first chamber 110 is kept at a preset temperature suitable for the dissolution of the Lewis catalyst, and the stirring speed of the agitator 3 is kept at the stirring speed suitable for the dissolution of the Lewis catalyst, such that the Lewis catalyst is quickly dissolved in the nitrobenzene, thereby greatly reducing the preparation time of the acylation liquid and improving the preparation efficiency of the acylation liquid.

In some embodiments, the preparation system further includes a heating device, a temperature sensor 5, and a controller. The heating device has a second inlet for the heat exchange medium and a second outlet for the heat exchange medium. The first outlet 1092 for the heat exchange medium is communicated with the second inlet for the heat exchange medium, and the first inlet 1091 for the heat exchange medium is communicated with the second outlet for the heat exchange medium.

The kettle body 1 has a temperature measuring port 105 communicated with the first chamber 110. Part of the temperature sensor 5 is hermetically inserted in the temperature measuring port 105, and a detection end of the temperature sensor 5 is located in the first chamber 110. The controller is connected to each of the heating device and the temperature sensor 5, and is configured to control the heating device according to a temperature detected by the temperature sensor 5.

In this way, the heat exchange medium heated by the heating device is introduced to the first inlet 1091 from the second outlet, and then is introduced into the jacket 109 through the first inlet 1091 to heat the materials in the first chamber 110. After heat exchange, the heat exchange medium in the jacket 109 flows out of the jacket 109 through the first outlet 1092, and is introduced into the heating device through the second inlet and may be heated by the heating device again, so as to realize a circulating flow of the heat exchange medium between the heating device and the kettle body 1.

The temperature sensor 5 may be used to detect the temperature of the material in the first chamber 110 in real time. A value of the temperature of the materials in the first chamber 110 detected by the temperature sensor 5 is transmitted to the controller, such that the controller may control the heating device. In some embodiments, when the temperature detected by the temperature sensor 5 is higher than the preset temperature, the controller controls the heating device to stop heating to prevent the material in the first chamber 110 from being overheated at a temperature higher than the preset temperature. When the temperature detected by the temperature sensor 5 is lower than the preset temperature, the controller controls the heating device to start heating to prevent the material in the first chamber 110 from being underheated at a temperature lower than the preset temperature. In this way, during the dissolution of the Lewis catalyst, the temperature in the first chamber 110 is kept at the preset temperature (range) suitable for the dissolution of the Lewis catalyst, which improves a dissolution rate of the Lewis catalyst and the preparation efficiency of acylation liquid.

In some embodiments, the model of the controller is DSC350.

In step c), a temperature of the mixture solution obtained in step b) is not higher than 60° C.

In the method for preparing the acylation liquid in the embodiments of the present disclosure, after the Lewis catalyst is dissolved in the solvent in step b), the mixture solution may be directly added with the acylation agent without an additional cooling treatment, which reduces energy consumption, shortens the preparation time of the acylation liquid and improves the preparation efficiency.

After the Lewis catalyst is dissolved in the solvent in step b), it is possible to cool the mixture solution by introducing the heat exchange medium (such as cooling water or coolant) into the jacket 109 through the first inlet 1091 for the heat exchange medium while using the feeding pump 6 to add the acylation agent into the first chamber 110.

As shown in FIG. 1 and FIG. 2, the preparation system 100 for preparing the acylation liquid further includes a pH meter 4. The kettle body 1 has a pH meter port 106 communicated with the first chamber 110. Part of the pH meter 4 is hermetically inserted in the pH meter port 106, and a detection end of the pH meter 4 is located in the first chamber 110.

In this way, the pH meter 4 may be used to detect a pH value of the material in the first chamber 110 in real-time, which improves the preparation efficiency of the acylation liquid and improves the quality of the prepared acylation liquid.

In some embodiments, the pH meter port 106 has a grinding port (which increases friction) to realize the sealing of the pH meter port 106.

For example, as shown in FIG. 3, an outside of the pH meter 4 is provided with a glass cover 10, the glass cover 10 has a tapered fitting surface 1001, and the fitting surface 1001 is sealed with the pH meter port 106.

In some embodiments, the pH meter 4 is SIN-PH6.3-5022-AL/Y-type pH meter.

In some embodiments, the preparation system 100 further includes a suction filtering device. The suction filtering device includes a filtering device 7, a liquid reservoir 8 and a vacuum pump 9.

The filtering device 7 includes a second shell 701 and a filtering membrane 702. The second shell 701 defines a second chamber, and the filtering membrane 702 is located in the second chamber. The filtering membrane 702 is used to divide the second chamber into a first part 7013 and a second part 7014. The second shell 701 has a filtering device inlet 7011 and a filtering device outlet 7012 both communicated with the second chamber. The first part 7013 is arranged adjacent to the filtering device inlet 7011, and the second part 7014 is arranged adjacent to the filtering device outlet 7012. The filtering device inlet 7011 is communicated with the liquid outlet 104.

The liquid reservoir 8 includes a third shell 801 defining the third chamber. The third shell 801 has a liquid reservoir inlet 8011 and a liquid reservoir outlet 8012. The liquid reservoir inlet 8011 is communicated with the filtering device outlet 7012. The vacuum pump 9 has a first vacuum pumping port 901. The second vacuum pumping port 8013 is located in the third shell 801 and communicated with the third chamber, and the first vacuum pumping port 901 is communicated with second vacuum pumping port 8013.

In some embodiments, the preparing the acylation liquid further includes: d) filtering the acylation liquid obtained in step c) in an inert gas atmosphere with the suction filtering device to obtain a filtered acylation liquid without solid particles. In the method for preparing acylation liquid in the embodiments of the present disclosure, the prepared acylation liquid is filtered under the inert atmosphere to remove all the undissolved solid particles in the liquid, which further improves the homogeneity of the liquid. Moreover, using the vacuum pump 9 forms a negative pressure in the filtering device 7, such that the acylation liquid in the kettle body 1 may quickly pass through the filtering membrane 702 of the filtering device 7 under the negative pressure and flow into the liquid reservoir 8 for storage, thereby further improving the overall preparation efficiency of the acylation liquid.

In some embodiments, as shown in FIG. 1, the first vacuum pumping port 901 is communicated with the second vacuum pumping port 8013 through a second pipe 900.

In some embodiments, during suction filtration, the first feeding port 101 may be communicated with an inert gas source to fill the preparation system with the inert gas, such that the prepared acylation liquid may be filtered under the inert atmosphere. In some embodiments, before adding the solvent to the first feeding port 101, the inert gas is introduced into the first shell 107, the second shell 701 and the third shell 801 through the first feeding port 101, such that the whole preparation process of the acylation liquid is performed under the inert atmosphere.

In some embodiments, the first shell 107, the second shell 701 and the third shell 801 are an integral structure. The liquid outlet 104 is located at a bottom of the first shell 107. The filtering device inlet 7011 is located at atop of the second shell 701, and the filtering device 7 is located below the kettle body 1. The filtering device outlet 7012 is located at a bottom of the second shell 701. The liquid reservoir inlet 8011 is located at atop of the third shell 801, and the liquid reservoir 8 is located below the filtering device 7.

In this way, the acylation liquid prepared in the kettle body 1 may be directly discharged from the kettle body 1 through the liquid outlet 104 by its own gravity to flow into the filtering device 7 through the filtering device inlet 7011. There is no need to arrange an additional liquid pump for pumping the acylation liquid between the liquid outlet 104 and the filtering device inlet 7011, and between the filtering device outlet 7012 and the liquid reservoir inlet 8011, which may simplify an overall structure of the preparation system 100 and reduce the manufacturing and operating costs of the preparation system 100. In addition, when the preparation system 100 is assembled, the connection between the liquid outlet 104 and the filtering device inlet 7011, and the connection between the filtering device outlet 7012 and the liquid reservoir inlet 8011 may be omitted to facilitate the assembly of the preparation system 100.

In some embodiments, each of the first shell 107, the jacket 109, the second shell 701 and the third shell 801 is formed of a high borosilicate glass material, which is convenient to observe situations in the kettle body 1, the filtering device 7 and the liquid reservoir 8.

In some embodiments, the preparation system 100 for preparing the acylation liquid further includes a first control valve 1041 located on the liquid outlet 104 to control opening and closing of the liquid outlet 104.

In this way, when the first control valve 1041 is opened, the prepared acylation liquid may be discharged from the kettle body 1 through the liquid outlet 104. When the first control valve 1041 is closed, the kettle body 1 is sealed, and the prepared acylation liquid is stored in the kettle body 1.

In some embodiments, the preparation system 100 for preparing the acylation liquid further includes a second control valve located on the liquid reservoir outlet 8012 to control opening or closing of the liquid reservoir outlet 8012.

In this way, when the second control valve is opened, the filtered acylation liquid is discharged from the liquid reservoir 8 through the liquid reservoir outlet 8012. When the second control valve is closed, the liquid reservoir 8 is sealed, and the filtered acylation liquid is stored in the liquid reservoir 8.

In some embodiments, a molar mass ratio of the acylation agent, the Lewis catalyst and the solvent is in a range of (1.1 to 1.5):(1.3 to 1.7):5, and/or a molar mass ratio of the Lewis catalyst to the solvent is in a range of 1.3:5 to 1.7:5. In other words, the molar mass ratio of the acylation agent, the Lewis catalyst and the solvent is in the range of (1.1 to 1.5):(1.3 to 1.7):5, and the molar mass ratio of the Lewis catalyst to the solvent is in the range of 1.3:5 to 1.7:5. Alternatively, the molar mass ratio of the acylation agent, the Lewis catalyst and the solvent is in the range of (1.1 to 1.5):(1.3 to 1.7):5, or the molar mass ratio of the Lewis catalyst to the solvent is in the range of 1.3:5 to 1.7:5.

In the method for preparing the acylation liquid in the embodiments of the present disclosure, the ratio of various materials is optimized, which may make full use of the raw materials and reduce the production cost.

Figure 12:
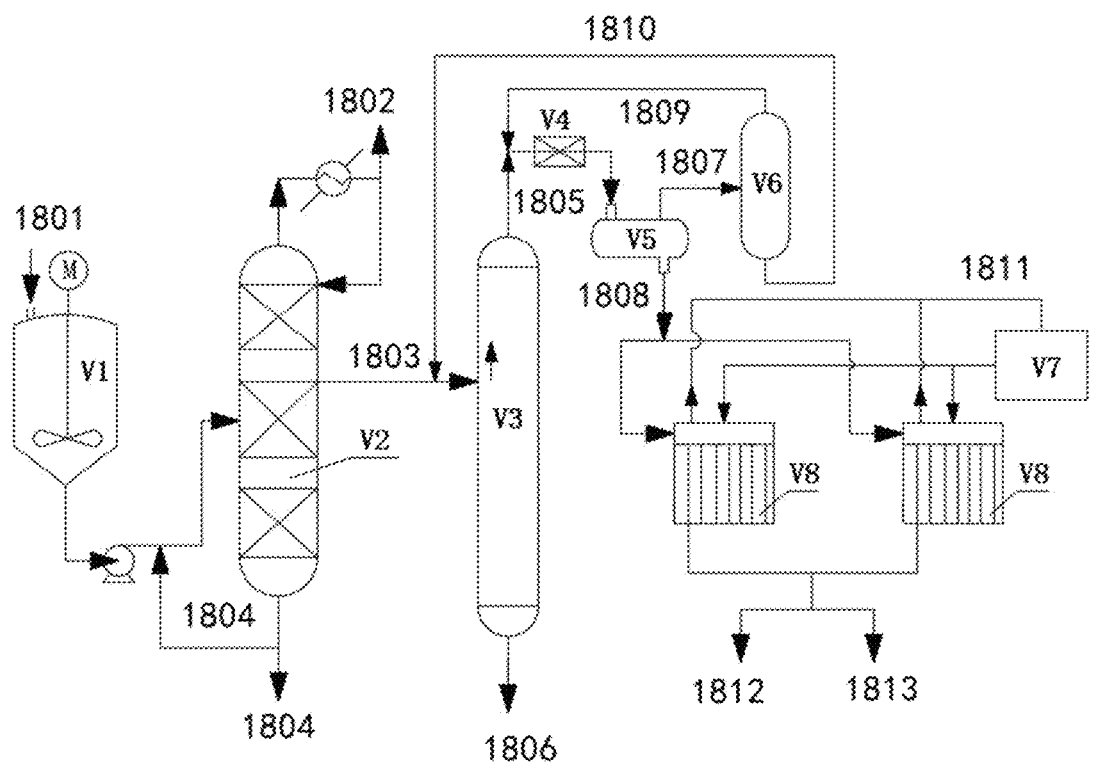
FIG. 12 is a process diagram showing extracting 2-methylnaphthalene from wash oil according to some embodiments of the present disclosure.

As shown in FIG. 12, in some embodiments, the prepared acylation liquid is used for continuous synthesis of acylnaphthalene by the following steps.

A raw material solution 14 is prepared. For example, in a case 5 L acylation liquid is applied, 700 g of nitrobenzene and 284 g of 2-methylnaphthalene are added into a reactor (containing the 5 L acylation liquid) equipped with a stirring device at the room temperature to prepare the raw solution 14. 2-methylnaphthalene has a purity of 99.0 to 99.9%, and is extracted from a wash oil by I) performing distillation and separation on the wash oil to obtain a methylnaphthalene-enriched fraction; II) introducing the methylnaphthalene-enriched fraction into an azeotropic rectification column for azeotropic distillation to obtain an azeotropic distillate; III) introducing the azeotropic distillate into a separator to obtain crude 2-methylnaphthalene; and IV) introducing the crude 2-methylnaphthalene into a plurality of batch melting crystallizers arranged in parallel for crystallization and purification to obtain the 2-methylnaphthalene.

In some embodiments, the wash oil refers to an oil used in scrubbing especially coke-oven gas for absorbing light oil and recovering benzene and other aromatic compounds. In step I), the wash oil is distilled and separated through an atmospheric rectification column to obtain a naphthalene light oil fraction, the methylnaphthalene-enriched fraction and a heavy oil fraction. Apart of the heavy oil fraction is returned back to the atmospheric rectification column, and the other part is recovered. The naphthalene light oil fraction is obtained from a top of the atmospheric rectification column, the methylnaphthalene-enriched fraction is obtained from a side line of the atmospheric rectification column, and the heavy oil fraction is obtained from a bottom of the atmospheric rectification column. A top temperature is in a range of 210° C. to 225° C., a side line temperature is in a range of 235° C. to 260° C., and a bottom temperature is in a range of 290° C. to 310° C.

In step II), the methylnaphthalene-enriched fraction and an azeotropic agent are mixed in a certain proportion, and are heated to a certain temperature to be introduced into the azeotropic rectification column for azeotropic distillation. The azeotropic agent is a one-compound type azeotropic agent or a mixture type azeotropic agent. The one-compound type azeotropic agent is any one of ethylene glycol, diethylene glycol, ethanolamine, diethylene glycol and N-methylformamide, and the mixture type azeotropic agent is a mixture of heptane and ethanolamine or a mixture of heptane and ethylene glycol. A top temperature of the azeotropic rectification column is in a range of 150° C. to 175° C., a top pressure is in a range of 1 to 4 KPa, and a reflux ratio (i.e., a ratio of an amount of liquid refluxed to an amount of distillate (overhead product)) is in a range of 5 to 15. A bottom temperature of the azeotropic rectification column is in a range of 220° C. to 245° C., and a bottom pressure is in a range of 10 to 15 KPa.

When the one-compound type azeotropic agent is used, a mass ratio of the methylnaphthalene-enriched fraction to the azeotropic agent is 1:1 to 3:1. When the mixture type azeotropic agent is used, a mass ratio of heptane to ethanolamine or a mass ratio of heptane to ethylene glycol in the mixture type azeotropic agent is 0.2:1 to 1:1. A mass ratio of the methylnaphthalene-enriched fraction to the azeotropic agent is 1:0.8 to 1:2. In step III), the azeotropic distillate and the water are introduced into an ultrasonic static mixer for ultrasonic mixing, and then are introduced into the separator for oil-water static separation to obtain a water phase and an oil phase. An operating temperature of the separator is in a range of 50° C. to 80° C., and a standing time is in a range of 0.2 to 1 hour. The water phase includes the azeotropic agent and the water, and the water phase is introduced into the rectification column for distillation and separation of the azeotropic agent and the water. The azeotropic agent after separation returns to step II) to mix with the methylnaphthalene-enriched fraction for recycling. The water after separation returns and is mixed with the azeotropic distillate for recycling. The oil phase includes the crude 2-methylnaphthalene, and is introduced into the batch melting crystallizers for crystallization and purification to obtain the 2-methylnaphthalene.

In step IV), two batch melting crystallizers are provided. During crystal growth, an initial temperature is in a range of 35° C. to 40° C. at a cooling rate in a range of 3° C./h to 8° C./h, and a final temperature is in a range of 8° C. to 12° C. and is kept for 0.5 h to 1 h. During sweating of the crystal, a heating rate is in a range of 2° C./h to 6° C./h, and a final temperature is in a range of 30° C. to 32° C. During melting of the crystal, a heating rate is in a range of 2° C./h to 8°

C./h, and a final temperature is in a range of 45° C. to 50° C. and is kept for 0.5 h to 1 h.

In some embodiments, the 2-methylnaphthalene is extracted from the wash oil by the following steps. The wash oil 1801 is added into a wash oil storage tank V1. After stirring and mixing, the wash oil 1801 is pumped into an atmospheric rectification column V2 for distillation and separation to obtain a naphthalene light oil fraction 1802 at a top of the column, and the naphthalene light oil fraction 1802 is used as a raw material for extracting naphthalene or may return back to the atmospheric rectification column V2. The methylnaphthalene-enriched fraction 1803 is obtained from a side stream. A bottom product from a bottom of the column is the heavy oil fraction 1804. Part of the heavy oil fraction 1804 may return back to the atmospheric rectification column V2, and the other part may be sent to a coal tar processing plant to further obtain acenaphthene, oxyfluorene, industrial fluorene and other products through separation. A top temperature of the atmospheric rectification column V2 is in a range of 210 to 225° C., a side stream temperature is in a range of 235 to 260° C., and a bottom temperature is in a range of 290 to 310° C. The obtained methylnaphthalene-enriched fraction 1803 and the azeotropic agent 1810 are mixed in a certain proportion, and are heated to a certain temperature to be introduced into the azeotropic rectification column V3 for azeotropic distillation. The azeotropic distillate 1805 is obtained from atop of the azeotropic rectification column V3, and is introduced into a separator to recycle the azeotropic agent 1810. Residual oil 1806 is obtained from a bottom of the column, and is discharged as a raw material for extracting other fine chemicals.

Since the azeotropic agent 1810 and the water 1809 have a high mutual solubility, the present disclosure adopts a process of water extraction to recover the azeotropic agent 1810. After the azeotropic agent distillate 1805 obtained in step II) is mixed with the water 1809, ultrasonic mixing is first performed in an ultrasonic static mixer V4, and then oil-water static separation is performed in a separator V5 to obtain a water phase and an oil phase from the separator. The water phase is an azeotropic agent mixture 1807 including the azeotropic agent 1810 and the water 1809, and the oil phase is crude 2-methylnaphthalene.

The water phase separated from the separator V5 is introduced into a rectification column V6 for distillation and separation of the azeotropic agent 1810 and the water 1809. After separation, the azeotropic agent 1810 obtained from a bottom of the column returns to step II) to mix with the methylnaphthalene-enriched fraction 1803 for recycling, and the water obtained from a top of the column returns to mix with the azeotropic distillate 1805 for recycling. The crude 2-methylnaphthalene 1808 separated from the separator V5 is purified through melting crystallization.

In addition, two batch melting crystallizers V8 are used in parallel to perform crystallization purification on the 2-methylnaphthalene alternately to achieve continuous crystallization purification. In the batch melting crystallizer V8, the crude methylnaphthalene 1808 is subjected to crystallization processes such as crystal growth, sweating and melting to realize the crystallization purification. After the crude methylnaphthalene 1808 is subjected to the melt crystallization purification, 2-methylnaphthalene product 1813 with a high purity is obtained. A liquid discharged during crystal growth and sweating is residual mother liquor 1812, which may be used as a raw material for extracting 1-methylnaphthalene. The purity of the 2-methylnaphthalene product 1813 after the crystallization and purification is 99.0 to 99.9%, and the product yield is 70% to 90%.

Figure 13:
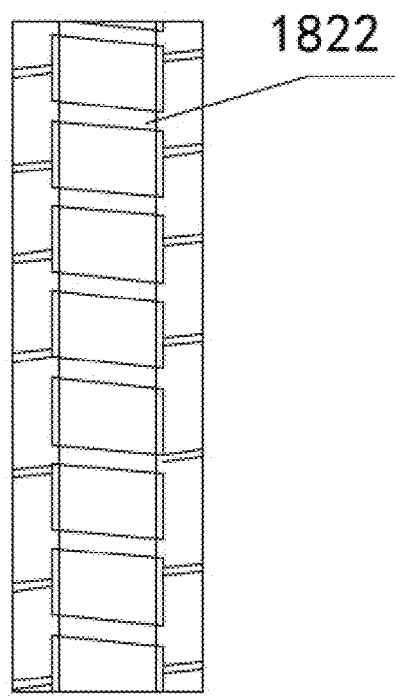
FIG. 13 is a schematic diagram showing a rectification column of an azeotropic rectification column.
Figure 14:
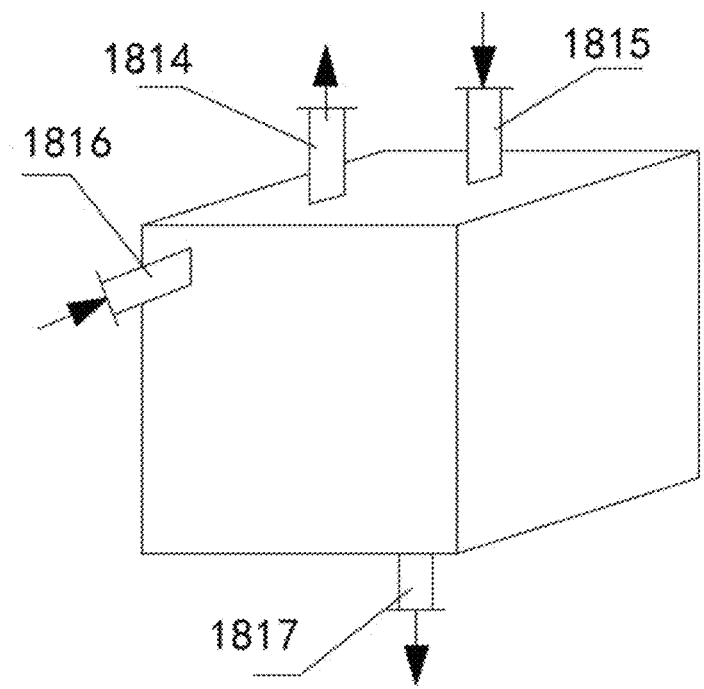
FIG. 14 is a schematic diagram showing a batch melting crystallizer.
Figure 15:
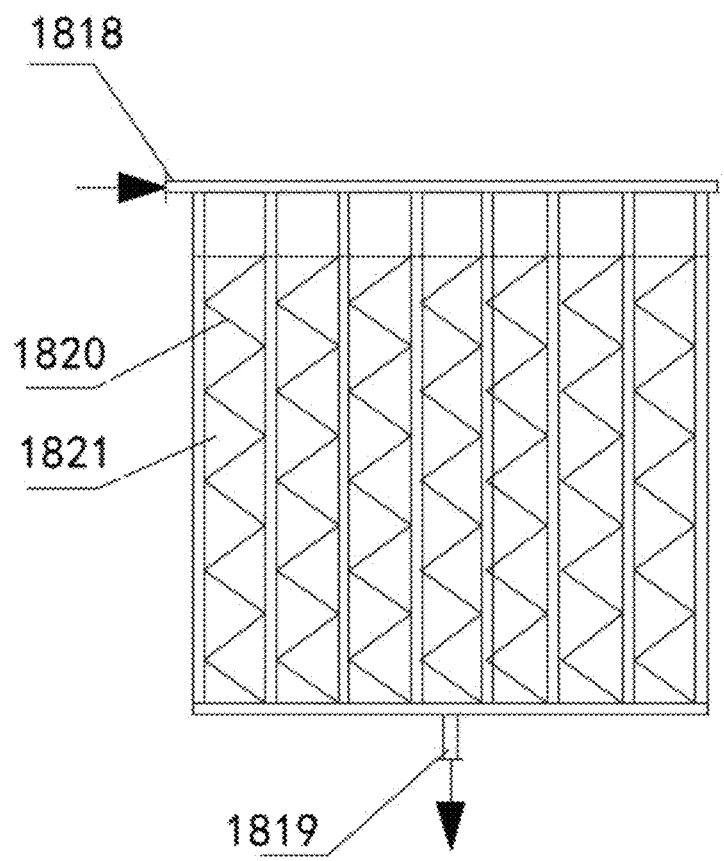
FIG. 15 is a schematic diagram showing a crystal plate.

In the above-mentioned process of extracting the 2-methylnaphthalene from the wash oil, the atmospheric rectification column V2 is a packed tower having a packing height theoretically equivalent to a stainless steel packed tower with 30 to 50 layers of tower plates. One part of the heavy oil fraction 1804 at the bottom of the column is recycled to be mixed with the wash oil, and then is introduced the atmospheric rectification column V2. Another part of the heavy oil fraction 1804 is discharged outside. A ratio of an amount of the heavy oil fraction that is discharged to an amount for recycling is in a range of 2:1 to 5:1. A content of the 2-methylnaphthalene in the methylnaphthalene-enriched fraction 1803 obtained is in a range of 50 to 70%. As shown in FIG. 13, the azeotropic rectification column V3 adopts a concentric pipe precision fractionating column composed of two pipes (being concentric) with exquisite design and precision calibration. A surface of an inner pipe is provided with a spiral groove 1822, which may improve a mass and heat transfer efficiency between a vertically rising steam and a liquid film in a gap between the concentric pipes. The azeotropic rectification column V3 is made of glass or stainless steel. The number of the theoretical plates of the fractionating column is in a range of 80 to 120. As shown in FIG. 14, the molten crystallizer is a full filled square static crystallizer having a cube shape and equipped with a first temperature control medium outlet 1814, a first temperature control medium inlet 1815, a material inlet 1816 and a material outlet 1817. In the molten crystallizer, there are several groups of mutually parallel crystal plates. As shown in FIG. 15, each group of the crystal plates is provided with coiled protrusions 1820. During crystallization, a crystal layer may grow on the protrusions 1820 and is not easy to fall off. During sweating, the crystal layer falls off from a growth surface of the crystal plate, and falls into a groove 1821 between the protrusions 1820 while keeping in contact with a heat exchange surface, which prevents the crystal layer from falling off easily during sweating. The heating and condensing medium (i.e., temperature control medium) flows inside the crystallization plate. The temperature control medium is introduced through a second temperature control medium inlet 1818 of the crystallization plate and passes through a second temperature control medium outlet 1819 of the crystallization plate to flow into a next group of the crystallization plates, and finally discharged through the temperature control medium outlet 1814 of the melt crystallizer. The crystal plate is made of stainless steel, organic glass or other alloys. Each batch melting crystallizer V8 is communicated with a digital temperature-controlled oil bath V7, and a heating and cooling medium 1811 is transmitted between the digital temperature-controlled oil bath V7 and the batch melting crystallizer V8.

Therefore, the embodiments of the present disclosure provide a method of the extraction of the high purity 2-methylnaphthalene from the coal tar wash oil, which is different from the traditional process using benzene-based compounds as the raw material and the process using naphthalene-based compounds, such as naphthalene and methylnaphthalene as the raw material to prepare 2,6-dimethylnaphthalene in the related art. In this way, the present disclosure improves the production efficiency, the product purity and the yield for the 2-methylnaphthalene separation and purification process, and reduces the pollution and equipment corrosion risks, thereby achieving a goal of synthesizing 2-methyl-6-propionylnaphthalene by using 2-methylnaphthalene as the raw material through the acylation and hydrolysis reactions with the acylation liquid, and a goal of the industrial production of 2-methyl-6-propionylnaphthalene by using a non-petroleum based route.

Figure 4:
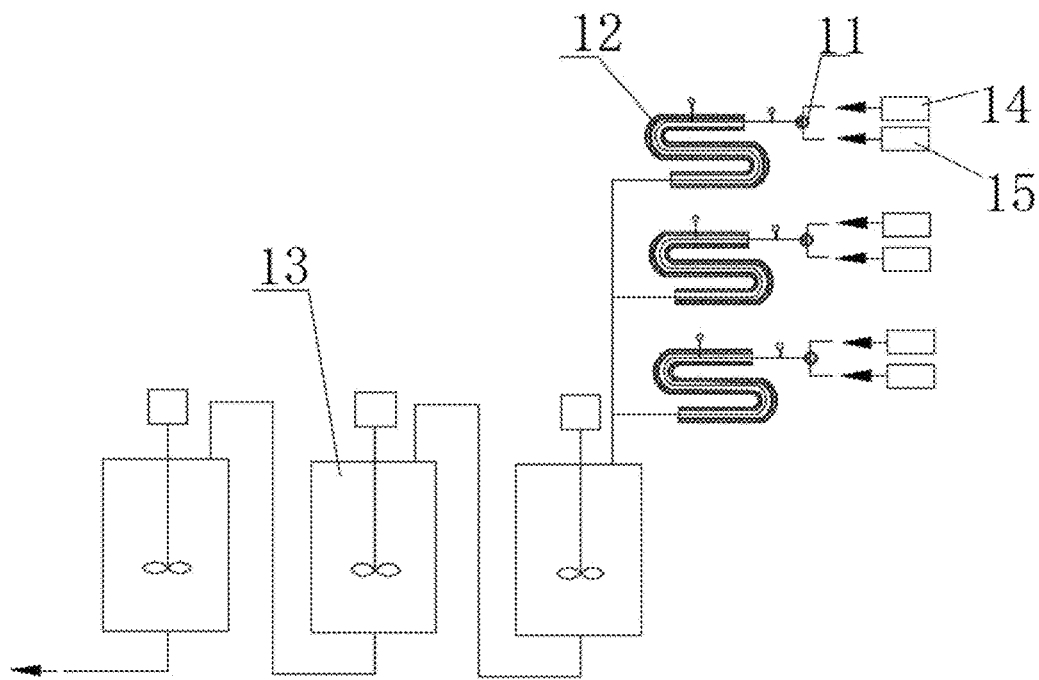
FIG. 4 is a schematic diagram showing an acylation reaction system according to some embodiments of the present disclosure.

As shown in FIG. 4, the prepared acylation liquid 15 and the raw solution 14 are subject to the acylation reaction. The raw solution 14 and the acylation liquid 15 are respectively sucked by a metering pump. A (metering pump) flow rate of the acylation liquid 15 is in a range of 158 to 162 g/min, and a (metering pump) flow rate of the raw solution 14 is in a range of 82 to 84 g/min. That is, a molar ratio of 2-methylnaphthalene: propionyl chloride: $AlCl_3$ is 1:1.3:1.5. The raw solution 14 and the acylation liquid 15 are injected into a three-way mixer 11 through a syringe, and are introduced, after mixing, into a microchannel reactor 12 for the reaction for 5 to 10 min to obtain an acylation reaction liquid. The acylation reaction liquid is introduced from a microchannel reactor outlet 12 into at least two kettle reactors 13 connected in series for reaction with stirring. After 2 to 4 kettle reactors 13, a total residence time of the acylation reaction liquid in the kettle reactor 13 is in a range of 50 to 80 min. The acylation reaction liquid discharged from the kettle reactor 13 is synchronously hydrolyzed, and is rectified to obtain 2-methyl-6-propionylnaphthalene.

A plurality of kettle reactors 13 is connected in series to realize continuous reaction. The flow rate is controlled through a regulating valve to control the residence time of the materials in the kettle reactor 13. A plurality of microchannel reactors 12 are provided and are connected in parallel with each other, and the flow rate of the acylation liquid 15 and the raw solution 14 is proportional to the number of the microchannel reactors 12 connected in parallel.

In some embodiments, the three-way mixer 11 and the microchannel reactor 12 are placed in a first thermostatic bath at a temperature of −5° C. to 0° C., and the temperature of the three-way mixer 11 and the microchannel reactor 12 is controlled at a temperature of −5° C. In some embodiments, the kettle reactor 13 is placed in a second thermostatic bath at a temperature of 30° C. to 50° C., and the temperature of the kettle reactor 13 is controlled at a temperature of 35° C.

There are two reasons for mixing the raw solution 14 and the acylation liquid 15 at the low temperature (i.e., in the three-way mixer 11 and the microchannel reactor 12), one is that a large amount of heat is released when two materials are mixed, and the low temperature is beneficial for the heat transfer, and the other one is that 60% to 70% of the raw material (2-methylnaphthalene) has been reacted in the acylation reaction at the low temperature, and this low temperature reaction can be well controlled kinetically.

In the art, the acylation reaction may happen in a batch kettle reactor or a continuous microchannel reactor only. The kettle reactor has a small heat exchange area (a reaction temperature therein is hard to control), an inconsistent residence time and an unstable product quality. The microchannel reactor has a high block risk, a high cost when the production is performed at a large scale and a complex operation. Therefore, the batch kettle reactor for the acylation reaction has disadvantages of a small heat exchange area (a reaction temperature therein is hard to control), an inconsistent residence time and an unstable product quality, and the continuous microchannel reactor for the acylation reaction has disadvantages of a high block risk, a high cost when the production is performed at a large scale and a complex operation. Therefore, compared with the related art, the acylation liquid and the raw material solution are mixed and reacted at the low temperature and are further reacted for a period of time with an increased temperature.

In some embodiments, the same raw solution pump is used to transport the raw material solution 14 to all the parallel microchannel reactors 12, and the same acylation liquid pump is used to transport the acylation liquid 15 to all the parallel microchannel reactors 12.

In some embodiments, the microchannel reactors 12 connected in parallel are directly connected with the plurality of kettle reactors 13 connected in series.

In some embodiments, the three-way mixer 11 is a T-type mixer or a Y-type mixer with an inner diameter of 0.5 mm to 3 mm.

In some embodiments, each of the microchannel reactor 12 and the kettle reactor 13 is formed of a strong acid corrosion-resistant material and has a good airtightness.

In some embodiments, an inner diameter of the microchannel reactor 12 is in a range of 0.5 to 3.175 mm.

In some embodiments, the acylating agent in the acylating liquid 15 is selected from any one of propionyl chloride, acetyl chloride, acetic anhydride or propionic anhydride.

In some embodiments, the acylation reaction liquid is directly introduced into a hydrolysis section for hydrolysis by the following steps. In the hydrolysis section, a water injection pump is started in advance, and water (deionized water) is introduced into a water phase pipeline of the hydrolysis section before introducing the acylation reaction liquid into the hydrolysis section. A flow rate of water in the water phase pipeline is controlled to 3 to 15 mL/min, for example 10 mL/min. After the water flows out of an outlet of the hydrolysis section, the acylation reaction liquid is introduced into an oil phase pipeline of the hydrolysis section through a one-way valve on the pipeline to mix with the water in a low temperature cold bath at a temperature of 0 to 20° C., for example 0° C. After the acylation reaction liquid is mixed, a mixed solution is introduced into a tubular reactor for the hydrolysis reaction at a temperature of 30 to 40° C., for example 30° C. An inner diameter of the tubular reactor is in a range of 2 to 5 mm. At the same time, an ultrasonic vibration is started to vibrate and stir the liquid in the tubular reactor, and an air suction pump (for example of the liquid separator 16) at an end is started. Since the inner diameter of the tubular reactor is 2 to 5 mm, the liquid may move slowly for 5 to 10 minutes from an inlet to an outlet of the tubular reactor to fully produce hydrolysis reaction.

After a turbid, light brown liquid (a mixed liquid after the hydrolysis reaction) flows out of the outlet of the tubular reactor, the separator 16 is used to collect the mixed solution. At this stage, the water is kept in a flowing state until the mixed solution is completely discharged, such that the hydrolysis reaction and the acylation reaction are simultaneously performed.

The separator 16 is a liquid-liquid separator. After the mixed solution is divided into different phases in the separator 16, the oil phase may be discharged from a lower port, and a measured pH value of the oil phase is 6 to 7. An upper end of the liquid separator 16 is communicated with the air suction pump through a pipeline, which may pump the waste gas (such as HCl) generated by the hydrolysis reaction to an alkali liquor tank downstream to collect the waste gas, thus avoiding air pollution.

After the acylation reaction, obtaining 2-methyl-6-acylnaphthalene with a high purity and yield may be affected by the hydrolysis process of the acylation reaction liquid containing 2-methyl-6-acylnaphthalene. Specifically, the hydrolysis process can stop the acylation reaction, remove aluminum chloride and the acylation agent, and dissolve HCl gas generated in the reaction, to keep 2-methyl-6-acylnaphthalene to be remained in the oil phase.

In the related art, the acylation reaction liquid may be hydrolyzed through the following processes. In a first process, the acylation reaction liquid is introduced into a mixer for storage, and after being mixed with water, it enters a microchannel reactor of a hydrolysis section downstream. In this process, the acylation reaction and the hydrolysis reaction cannot be performed simultaneously, as a large amount of heat will be released when the acylation reaction liquid contacts with water, which is difficult be cooled down in a short time. In a second process, the product after reaction is introduced into a hydrolysis reactor, and the mixed reaction liquid is poured into a beaker filled with ice while being continuously stirred mechanically. Distilled water is added for the hydrolysis while being stirred for another half an hour to completely hydrolyze the acylation product. This process is a batch hydrolysis reaction that takes a long time, which is complex in operation and has a general hydrolysis effect.

However, the related art adopts the batch or semi-continuous hydrolysis, but no synchronous, i.e., continuous hydrolysis is disclosed. That is, the existing process needs to obtain the acylation reaction liquid first, and there is a certain time interval between obtaining the acylation reaction liquid and the hydrolysis reaction. In this case, the acylation reaction liquid cannot be hydrolyzed in time, and is easy to be reacted with water in the air during waiting to generate HCl gas that pollutes the air. $Al(OH)_3$ emulsion will be produced during the hydrolysis reaction. The microchannel reactor may be used for the hydrolysis reaction, and in this case a channel/pipeline thereof may be blocked when the acylation reaction liquid contacts with water. The hydrolysis reaction is exothermic. Pressure is increased in the channel of the hydrolysis section due to the instantaneously-released heat, and a small amount of acid gas volatilizes. A large volume of turbid liquid is obtained through the hydrolysis, and separation/purification for this liquid is complex and time-consuming.

Figure 5:
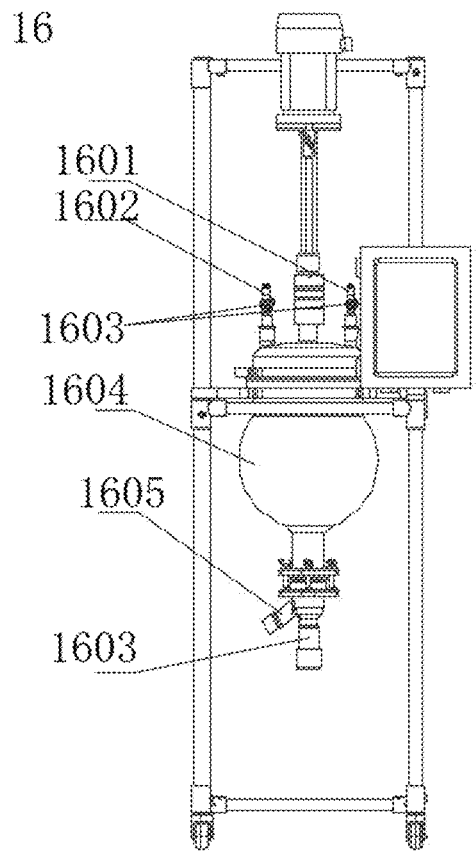
FIG. 5 is a schematic diagram showing a liquid separator according to some embodiments of the present disclosure.

In some embodiments, as shown in FIG. 5, the liquid separator 16 includes a container 1604, a stirring device, a feeding inlet 1602, a discharge outlet 1605, and an exhaust outlet 1601. The stirring device extends into the container 1604, and the stirring device is connected to an external reducer for driving. The stirring device is not shown in this drawing, and the stirring device has a common structure, which will be not described here. The discharge outlet 1605 is communicated with a bottom end of the container 1604, and the feeding inlet 1602 and the exhaust outlet 1601 are communicated with an upper end of the container 1604. The feeding inlet 1602 is communicated with the outlet of the tubular reactor in the hydrolysis section through a pipeline, and the exhaust outlet 1601 is communicated with a suction pump through a pipeline. The feeding port 1602, the discharging port 1605 and the exhaust port 1601 are provided with control valves 1603. The control valve 1603 at the discharging port 1605 is kept closed until the water phase and the oil phase are layered and the oil phase is ready to be discharged. The water phase and the oil phase are separated in layers. The oil phase is below the water phase. The oil phase is discharged first from the discharging outlet 1605. The oil phase may contain some water, and may be purified through distillation.

It should be noted here that the container 1604 of the liquid separator 16 has an enough space and an effective volume of 10 L, which ensures that the liquid separator 16 will not be full. The inner diameter of the channel in the tubular reactor is very small, and the liquid moves slowly. Even when the mixed liquid completely flows into the liquid separator 16, the liquid separator 16 will not be filled up. A tolerance temperature of the liquid separator 16 is −80 to 200° C., that is, the liquid separator 16 will not be damaged when it is used at such a temperature.

In some embodiments, the one-way valve is a stainless steel ferrule check valve, and an internal flow channel is made of polytetrafluoroethylene, which has anti-corrosion performance. The flow channel in the traditional one-way valve is made of ordinary rubber or corrosion-resistant rubber. However, after the test, its corrosion resistance effect is not good, and thus it is replaced with polytetrafluoroethylene material to greatly improve the corrosion resistance.

In the process of synchronous hydrolysis, the water pump is first turned on, and then the acylation reaction liquid flowing out of the kettle reactor 13 is immediately introduced into the hydrolysis section for continuous and stable hydrolysis, which may greatly improve the hydrolysis efficiency and material balance rate.

In the present disclosure, the acylation reaction is synchronized with the hydrolysis reaction, which avoids temporary storage of the acylation reaction liquid and reduces the HCl gas escape and pollution.

The hydrolysis reaction is an exothermic reaction. It should be mixed with the water quickly in the low temperature cold bath (0° C.) before entering the tubular reactor, which may rapidly reduce the hydrolysis temperature.

When the tubular reactor is used for the hydrolysis reaction, the one-way valve is provided in a front section of the pipeline where the acylation reaction liquid and the water converge to prevent the liquid from flowing back to the acylation section from the hydrolysis section, thereby avoiding blockage of the channel of the tubular reactor.

The obtained liquid after the hydrolysis reaction may be directly introduced through an upper end of the liquid separator 16 for synchronous separation. The oil phase may be discharged from a lower port. The measured pH value of the hydrolyzed oil phase is 6 to 7, which meets the purification requirements.

In the hydrolysis process, the acylation reaction liquid flowing out of the tubular reactor is immediately introduced into the hydrolysis section for the continuous and stable hydrolysis, which improves the material balance, and avoids the blockage. The obtained liquid after the hydrolysis reaction may be directly introduced into the liquid separator 16 for the synchronous separation. The oil phase may be conveniently discharged from the lower port for the rectification and crystallization to obtain 2-methyl-6-propionylnaphthalene. The generated waste gas may be sucked from an upper end of the exhaust outlet 1601 of the liquid separator 16. The water phase is treated by the treatment process of the acylation wastewater.

Figure 6:
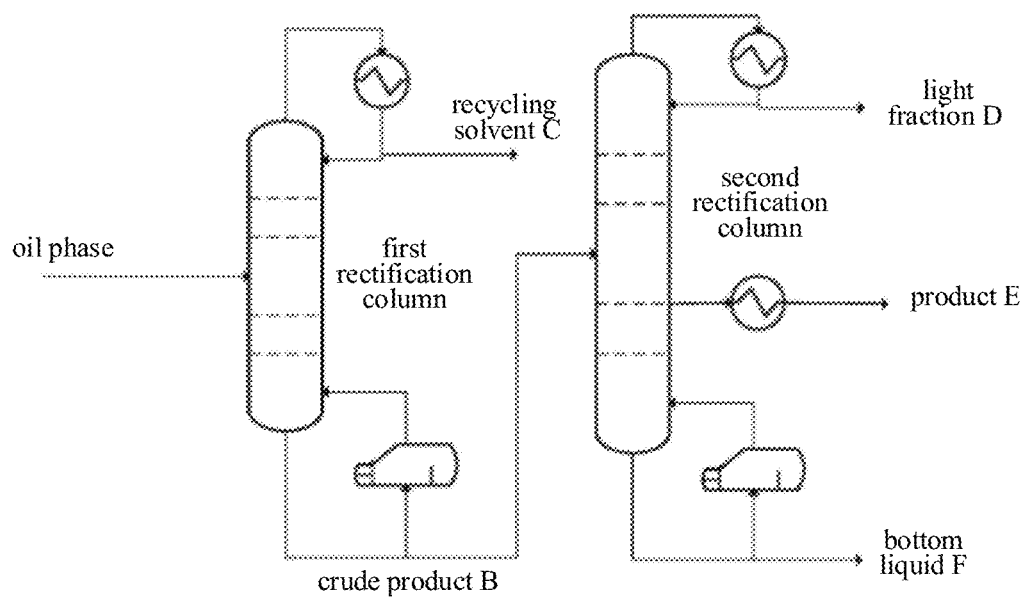
FIG. 6 is a process diagram showing a rectification process according to some embodiments of the present disclosure.

In some embodiments, a process for rectifying the oil phase separated by the hydrolysis reaction is provided. As shown in FIG. 6, the process includes the following steps.

(1) The oil phase separated by the hydrolysis reaction is fed into a middle of the first rectification column for distillation. A first light fraction is discharged from a top of the first rectification column, and the first light fraction after condensation is recycled. A bottom liquid is discharged from a bottom of the first rectification column.

In some embodiments, the oil phase separated by the hydrolysis reaction is introduced into the first rectification column. The first rectification column is a light fraction removing column, and adopts a filler selected from ceramic fillers, spring fillers, O-ring fillers or any combination thereof. The light distillate at the top of the light fraction removing column is a small amount of water, and it may be recovered after condensation and recycled into the wastewater for advanced oxidation treatment. Nitrobenzene is collected as a side stream of the light fraction removing column, and may be recycled for reuse. The bottom liquid discharged from the bottom of the light fraction removing column is the crude product and flows into the second rectification column.

In some embodiments, the first rectification column has a pressure in a range of 0.05 KPa to 10 KPa and a reflux ratio in a range of 1:1 to 2:1. In some embodiments, the first rectification column has a pressure in a range of 0.1 KPa to 2 KPa.

In some embodiments, a condensation temperature of the first rectification column is in a range of 10° C. to 20° C. In some embodiments, the condensation temperature of the first rectification column is in a range of 10° C. to 15° C.

(2) The bottom liquid in step (1) (maintained at a relatively high temperature) is pumped to a second rectification column for further distillation. A second light fraction of the second rectification column is discharged from atop of the second rectification column, and the second light fraction after condensation is collected. A product from a side stream of the second rectification column is collected. A heavy bottom fraction from the second rectification column is heated with a reboiler, and the heavy bottom fraction (maintained at a relatively high temperature) is pumped to a bottom collection tank.

In some embodiments, the second rectification column is a heavy fraction removing column. A filler in the heavy fraction removing column may include ceramic fillers, spring fillers, O-ring fillers or any combination thereof. A light fraction of isomers other than 2-methyl-6-propionylnaphthalene (2,6-MPN) from the top of the heavy fraction removing column is recovered after condensation. A small amount of heavy colored impurities is discharged from a bottom of the heavy fraction removing column for regular collection and post-treatment. The crude product 2,6-MPN fraction of the acylation section is extracted from the side stream of the heavy fraction removing column and sent to a recrystallizer after cooling. An acyl group of 2-methyl-6-acylnaphthalene other than 2,6-MPN is one of methyl, ethyl, or isopropyl group. That is, the product 2-methyl-6-acylnaphthalene is selected from 2-methyl-6-formylnaphthalene, 2-methyl-6-acetylnaphthalene, or 2-methyl-6-isopropylnaphthalene.

In some embodiments, the second rectification column has a pressure in a range of 0.05 KPa to 10 KP and a reflux ratio in a range of 5:1 to 10:1. In some embodiments, the second rectification column has a pressure in a range of 0.1 KPa to 2 KPa.

In some embodiments, a condensation temperature of the second rectification column is in a range of 50° C. to 90° C. In some embodiments, a condensation temperature of the second rectification column is in a range of 70° C. to 90° C.

In some embodiments, a process for recrystallization of the crude product 2,6-MPN includes the following steps. A methanol solution (with a mass ratio of methanol to water of 85:15) is mixed with the crude product 2,6-MPN at a mass ratio of 8:1 in a three necked flask equipped with a stirrer, a thermometer and a reflux condenser pipe, and then the flask is put in a water bath and the solution is stirred at a temperature of 55° C. until a light yellow solid is completely dissolved. After stirring for another 20 minutes, the solution is recrystallized at a temperature of 10° C. for 6 hours. After the crystallization is completed, suction filtration and solid-liquid separation are performed to obtain fine white 2-methyl-6-propionylnaphthalene powders. The product is placed in a dryer to remove the solvent. The 2,6-MPN slurry obtained by the recrystallization is separated into a filter cake and a filtrate by a filter, in which a mother liquor and a washing liquor are introduced into a methanol recovery column. Methanol obtained from a top of the methanol recovery column may be reused, and a bottom product from a bottom of the methanol recovery column is discharged into the wastewater system. The wet filter cake is dried by a dryer. The exhaust gas from the dryer is introduced into the methanol recovery system, and the product 2,6-MPN is obtained after drying.

In addition, the water phase separated from the liquid separator 16 is treated by the following treatment process of the acylation wastewater.

Wastewater after the acylation reaction is an organic liquid with a high toxicity and a high salt content (as shown in Table 1), which is difficult to be biodegraded. With the high level environmental requirements, the industrialization and application of Friedel-Crafts acylation reaction is limited by the organic wastewater generated during the acylation reaction.

TABLE 1 water quality of acylation wastewater

| item | pH | total solution | chloride ion | COD | aluminium ion | nitrobenzene |
|---|---|---|---|---|---|---|
| value | 1-3 | 10000-30000 mg/L | 3000-10000 mg/L | 5000-10000 mg/L | 1000-5000 mg/L | 1000-5000 mg/L |

The present disclosure provides a process for treating the organic wastewater that generated from the acylation reaction.

Figure 7:
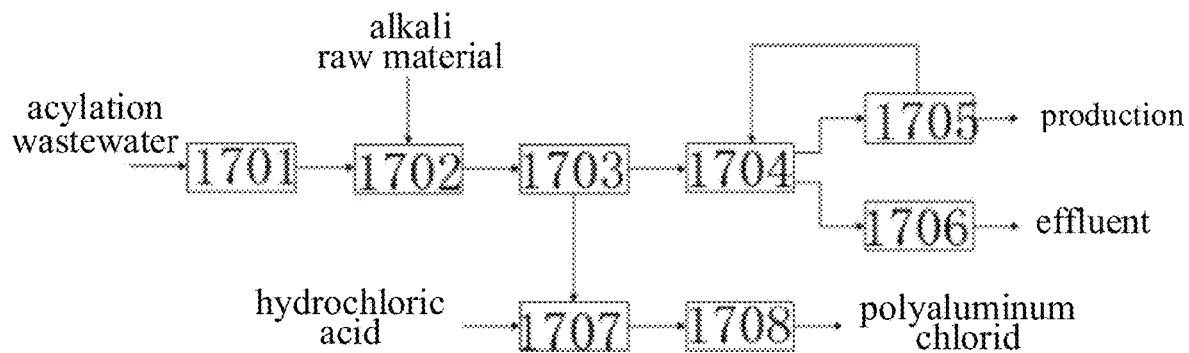
FIG. 7 is a process diagram of a recyclable treatment process of a water phase separated by a liquid separator according to some embodiments of the present disclosure.

As shown in FIG. 7, a resource recoverable acylation wastewater treatment system in embodiments of the present disclosure includes a sedimentation tank 1702, a filtering unit 1703, an extraction unit 1704, a rectification column 1705, a biochemical treatment unit 1706, a dissolution tank 1707 and a reaction kettle 1708. The sedimentation tank 1702 is configured to generate aluminum hydroxide precipitation. An inlet of the filtering unit 1703 is communicated with an outlet of the sedimentation tank 1702. An inlet of the extraction unit 1704 is communicated with an outlet of the filtering unit 1703. The extraction unit 1704 is provided with an extractant inlet. An inlet of the rectification column 1705 is communicated with an extraction phase outlet of the extraction unit 1704. The rectification column 1705 is provided with an extractant outlet communicated with the extractant inlet of the extraction unit 1704, and a nitrobenzene outlet communicated with an organic solvent pipeline for production. An inlet of the biochemical treatment unit 1706 is communicated with a raffinate outlet of the extraction unit 1704, and an outlet of the biochemical treatment unit 1706 is communicated with a wastewater meeting the standard discharge pipeline. An outlet of the dissolution tank 1707 is communicated with a filter cake outlet of the filtering unit 1703, and the dissolution tank 1707 is provided with a concentrated hydrochloric acid inlet. An inlet of the reaction kettle 1708 is communicated with the outlet of dissolution tank 1707.

In some embodiments, the extraction unit 1704 is a centrifugal extraction device, such as a commercially available centrifugal extractor.

Figure 8:
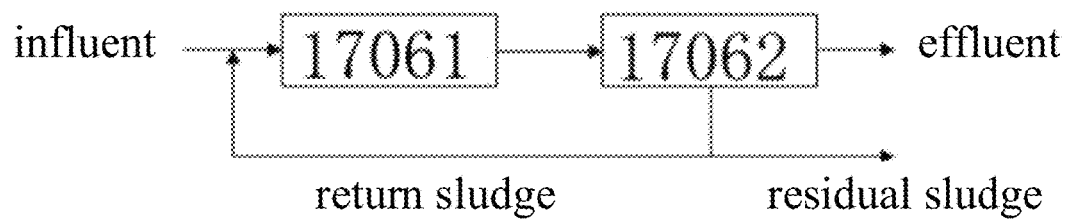
FIG. 8 is a schematic diagram showing an activated sludge treatment system.

In some embodiments, the biochemical treatment unit 1706 may adopt an activated sludge treatment system. The activated sludge system may adopt a conventional activated sludge treatment system, which will not be described in detail here. As shown in FIG. 8, the activated sludge treatment system includes an aeration tank 17061, a secondary sedimentation tank 17602, a reflux system, a residual sludge discharge system, and an oxygen supply system. In some embodiments of the present disclosure, the extraction phase outlet of the extraction unit 1704 is communicated with the water inlet of the aeration tank 17061, such that the extraction phase may be introduced into the activated sludge treatment system, and be treated according to the conventional activated sludge process to meet a discharging standard.

It should be noted that, in the resource recoverable acylation wastewater treatment system in the embodiments of the present disclosure, the connection/communication between the devices may be realized through pipeline connection or transportation of transfer vehicles according to the nature of the materials. In the case of pipeline connection, valves and pumps may be installed on the corresponding pipelines as required, which is not described in detail in the present disclosure.

In some embodiments, in order to control water volume, balance water quality and pretreat the acylation wastewater, the resource recoverable acylation wastewater treatment system of the embodiments in the present disclosure further includes a regulation tank 1701 located in front of the sedimentation tank 1702. The acylation wastewater is first introduced into the regulation tank 1701 to adjust water volume, water quality of the wastewater and to perform pretreatment, and then is introduced into the sedimentation tank 1702.

In some embodiments, the reaction kettle may be formed of a stainless steel material. The sedimentation tank 1702 may be a horizontal flow sedimentation tank or a vertical flow sedimentation tank. The filtering unit 1703 may be a plate and frame filter. The dissolution tank may be a common dissolution tank. The rectification column may be a packed column or a plate column.

The resource recoverable acylation wastewater treatment system in the embodiments of the present disclosure may be operated as follows.

The water phase is first introduced into the regulation tank 1701 to regulate water volume, balance water quality and perform pretreatment, and then is introduced into the sedimentation tank 1702. The acylation wastewater introduced in the sedimentation tank 1702 is adjusted in alkalinity to a pH value of 8 to 10 by at least one of the alkali sources of sodium hydroxide, potassium hydroxide and liquid ammonia. In some embodiments, the pH value is adjusted to about 9. Aluminum ions in the acylation wastewater are precipitated into aluminum hydroxide. The suspension containing aluminum hydroxide precipitation is filtered through the filtering unit 1703 to obtain an aluminum hydroxide filter cake and a filtrate. A pH value of the filtrate is adjusted to 2 to 3 with at least one of hydrochloric acid, nitric acid and sulfuric acid, and then the filtrate is introduced into the extraction unit 1704. The filtrate is subjected to extraction with an extractant in the extraction unit 1704 to obtain a raffinate phase and an extraction phase after stirring and standing. The extractant is a non-polar organic solvent, which is at least one of n-heptane, n-octane, n-hexane, benzene, toluene, xylene and carbon tetrachloride, and a volume ratio of the extractant to the filtrate is in a range of 0.5:1 to 5:1.

The extraction phase is introduced into the rectification column 1705 for efficient separation of nitrobenzene and the extractant to obtain nitrobenzene and the extractant. The extractant from the rectification column 1705 is introduced back to the extraction unit 1704 for the extraction. The nitrobenzene from the rectification column 1705 is introduced into a production organic solvent pipeline for production of related chemicals. The raffinate from the extraction unit 1704 is introduced into a biochemical treatment unit 1706 for biochemical treatment, and then is discharged after reaching a discharging standard. The aluminum hydroxide filter cake from the filtering unit 1703 is introduced into the dissolution tank 1707, and is dissolved with concentrated hydrochloric acid and heated at a temperature of 40° C. to 50° C. in the dissolution tank 1707 to obtain a solution. A weight ratio of the filter cake to the concentrated hydrochloric acid is 0.5:1 to 2.5:1. The solution is introduced into the reaction kettle 1708, and polymerized with an additive in the reaction kettle 1708 to obtain a polyaluminum chloride which is a water treatment agent. A quality of the obtained polyaluminum chloride meets a standard of polyaluminum chloride "GB/T22627-2014 Water treatment chemical-Polyaluminium chloride". The additive is calcium aluminate and/or magnesium aluminate, and an addition amount is in a range of 2 to 10 wt % based on a weight of the filter cake.

It should be noted that the resource recoverable acylation wastewater treatment process in the embodiments of the present disclosure may be used to treat the acylation wastewater and recover its resources with the resource recoverable acylation wastewater treatment system of the embodiments in the present disclosure, but the treatment process may be implemented by other systems, which is not limited to the resource recoverable acylation wastewater treatment system in the embodiments of the present disclosure.

The resource recoverable acylation wastewater treatment process in the embodiments of the present disclosure is described below in combination with the following embodiments.

Unless specified otherwise, the raw materials, the agents and the device in the embodiments of the present disclosure are commercially available reagents and devices. The detection methods in embodiments of the present disclosure are common methods unless otherwise specified.

The following embodiments of the present disclosure are implemented under laboratory conditions, and the suction filtering device may be a laboratory suction filtering device composed of a Buchner funnel, a suction filtration bottle, a rubber pipe, an air suction pump and a filter paper.

The method for preparing the acylation liquid in the embodiments of the present disclosure is described in detail below in combination with the following examples.

Example 1

<Preparation of Acylation Liquid>

600.4 g of nitrobenzene is added into a three necked flask, and 200.41 g of aluminum chloride is weighed under nitrogen protection to be added to the nitrobenzene in the first chamber 110. The nitrobenzene and the aluminum chloride are heated to 60° C. by using the heat exchange medium and is stirred at a stirring speed of 300 rpm with the agitator 3, obtaining a mixture solution. Under a condition that a temperature of the mixture solution is 50° C., 120.13 g of a propionylation agent is pumped by the feeding pump 6 into the mixture solution at a speed of 5 drops per second and a stirring speed of 300 rpm. After the addition of the propionylation agent is completed, an acylation liquid is obtained. Under the nitrogen protection, the acylation liquid is filtered by a suction filtering device to remove solid particles in the acylation liquid to further refine the acylation liquid, and the acylation liquid is stored in a liquid reservoir for 30 days with a solid content of less than 0.2%.

<Continuous Synthesis of Acylnaphthalene by Acylation Liquid>

A raw solution 14 and the acylation liquid 15 in Example 1 is respectively sucked through a corresponding metering pump. A (metering pump) flow rate of the acylation liquid 15 is 160 g/min, and a (metering pump) flow rate of the raw solution 14 is 83 g/min. That is, 2-methylnaphthalene, propionyl chloride and $AlCl_3$ are mixed at a molar ratio of 1:1.3:1.5 to obtain an acylation reaction liquid. The two materials 14 and 15 are injected into the three-way mixer 11 with an inner diameter of 3 mm through a syringe for mixing. After mixing, the two materials are added into a microchannel reactor 12 with an inner diameter of 3 mm for reaction. After 5 minutes, the acylation reaction liquid flows out of an outlet of the microchannel reactor 12 and flows into the plurality of the kettle reactors 13 connected in series. The three-way mixer 11 and the microchannel reactor 12 are placed in a first thermostatic bath, and a first reaction temperature is controlled at −5° C. The kettle reactor 13 is placed in a second thermostatic bath, and a second reaction temperature is controlled at 40° C. The acylation reaction liquid is stirred in kettle reactor 13 for reaction. A total residence time of the acylation reaction in the three kettle reactors 13 is 60 min, and the acylation reaction liquid flowing out of the kettle reactor 13 is introduced into the tubular reactor, and mixed with demineralized water for hydrolysis reaction.

The hydrolysis reaction process is performed in the tubular reactor by the following steps. During the hydrolysis section, the water injection pump is turned on in advance. Before the acylation reaction liquid is introduced to the hydrolysis section, deionized water is introduced into the water phase pipeline of the hydrolysis section, and a flow rate of the water in the water phase pipeline is controlled to 10 mL/min. After the water flows out of the outlet of the hydrolysis section, the acylation reaction liquid flowing out of the kettle reactor 13 is introduced into the oil phase pipeline of the hydrolysis section through the one-way valve arranged on the pipeline. The acylation reaction liquid is quickly mixed with the water in a low temperature cold bath at 0° C. and then be introduced into the tubular reactor. The hydrolysis reaction is performed at a temperature of 30° C. At the same time, an ultrasonic vibration is turned on to vibrate and stir the liquid in the tubular reactor, and an air pump of the liquid separator 16 at an end is turned on. The acylation reaction is terminated, and the obtained hydrolysate is introduced into the liquid separator 16. Under stirring at 80° C. in the liquid separator 16 for 4 hours, the oil phase and the water phase are separated. The separated oil phase solution is to be rectified, and the water phase solution is transmitted to a wastewater treatment plant after advanced oxidation treatment of wastewater. 2-methylnaphthalene obtained has a conversion rate of more than 99.0%, and a selectivity of 88.0%.

As shown in FIG. 6, a process for rectifying the oil phase separated by the hydrolysis reaction includes the following steps.

(1) The oil phase is fed into a middle of a first rectification column for distillation. The acylation reaction liquid contains 80 wt % nitrobenzene solvent and 20 wt % crude 2-methyl-6-propionylnaphthalene fraction. A pressure of the first rectification column is 0.1 kPa, a rectification temperature is 45° C. to 130° C. The nitrobenzene is discharged from a top of the first rectification column at a temperature of 45° C. at a reflux ratio of 1:1. A top condensation temperature is 10° C., and the nitrobenzene solvent C is recovered from the top by cooling the gas phase nitrobenzene recovered at the top. A temperature of a bottom liquid B is 130° C., and the bottom liquid is discharged from a bottom of the first rectification column. After rectification performed in the first rectification column, 98% of nitrobenzene solvent C is recovered, and the bottom liquid B contains 78% crude 2-methyl-6-propionylnaphthalene.

(2) In step (1), a discharge temperature of the bottom liquid B is 130° C., and the bottom liquid still hot is pumped to a second rectification column for further distillation. A pressure of the second rectification column is 1 kPa, a distillation temperature is in a range of 110 to 150° C., a reflux ratio is in a range of 5:1, and a condensation temperature is 75° C. 17 wt % of a light isomer D of 2-methyl-6-propionylnaphthalene is discharged from a top at a temperature of 114° C., and is collected after condensation. 80 wt % of the product E of 2-methyl-6-propionylnaphthalene is discharged from a side stream of the second rectification column (i.e., flows out of the second rectification column through a middle outlet) at a temperature of 136° C. 3 wt % of heavy bottom fraction F is discharged from a bottom of the second rectification column and is introduced and heated with a reboiler, and the heavy bottom fraction still hot is pumped to a bottom collection tank by a heat pump.

The number of theoretical plates of the first rectification column is 30, and a feeding position is located at the 15th theoretical plate. The number of theoretical plates of the second rectification column is 40, the feeding position is located at the 25th theoretical plate, and the product side stream is located at the 22nd theoretical plate.

A process for recrystallization of the crude product 2,6-MPN is as follows. A methanol solution (with a mass ratio of methanol to water of 85:15) is mixed with the crude product 2,6-MPN at a mass ratio of 8:1 in a three necked flask equipped with a stirrer, a thermometer and a reflux condenser pipe, and then the flask is put in a water bath and the solution is stirred at a temperature of 55° C. until a light yellow solid is completely dissolved. After stirring for another 20 minutes, the solution is recrystallized at a temperature of 10° C. for 6 hours. After the crystallization is completed, suction filtration and solid-liquid separation are performed to obtain fine white 2-methyl-6-propionylnaphthalene powders. The product is placed in a dryer to remove the solvent. The 2,6-MPN slurry obtained by the recrystallization is separated into a filter cake and a filtrate by a filter, in which a mother liquor and a washing liquor are introduced into a methanol recovery column. The methanol from a top of the methanol recovery column is reused, and a bottom product from a bottom of the methanol recovery column is discharged into a wastewater system. The wet filter cake is dried by a dryer. The exhaust gas from the dryer is introduced into the methanol recovery system, and the product 2,6-MPN is obtained after drying.

The acylation liquid prepared in the process of Example 1 is mixed with the prepared 2-methylnaphthalene raw solution 14, and the acylation reaction is performed in a reactor combining a microchannel rector with a kettle rector. After the reaction, hydrolysis, vacuum distillation and recrystallization are performed. The 2-methyl-6-propionylnaphthalene product with a yield of 80% and a purity of 98.0% is obtained.

In Examples (IEs) 2 to 7 and Comparison Examples (CEs) 1 to 10 are substantially the same with Example 1, except that some adjustments in conditions such as the preparation of the acylation liquid, the acylation hydrolysis reaction conditions and the oil phase distillation process as shown in Table 2. Table 2 also shows a quality of the acylation liquid (i.e., a solid content after the liquid is stored in the liquid reservoir for 30 days) obtained in each of IEs 2-7 and CEs 1-10. Yield and purity of the 2-methyl-6-propionylnaphthalene product obtained after the recrystallization, and conversion rate and selectivity of 2-methylnaphthalene obtained after the acylation reaction and the hydrolysis are recorded in Table 3.

TABLE 2 different conditions of Examples 2-7 and Comparative Examples 1-10

| | Acylation solution preparation | Acylation reaction & hydrolysis | Oil phase distillation | Solid |
|---|---|---|---|---|
| IE2 | The suction filtering device is not used. | / | / | >0.5% |
| IE3 | / | / | Oil phase includes 77 wt % nitrobenzene solvent and 23 wt % crude fraction of 2-methyl-6-propionyl-naphthalene. A pressure of a first rectification column is 0.6 KPa, a rectification temperature is 60 to 150° C., and nitrobenzene is discharged from a top of the column at 60° C.. A temperature of bottom liquid B is 150° C.. The bottom liquid B is discharged at a temperature of 140° C.. In the second rectification column, a pressure is 0.6 KPa, a distillation temperature is 140 to 180° C., a reflux ratio is 5:1, a condensation temperature is 70° C.. | <0.2% |
| IE4 | / | The first reaction temperature is controlled at −3° C., and the second reaction temperature is controlled at 50° C.. | / | <0.2% |
| IE5 | / | The first reaction temperature is controlled at 0° C., and the second reaction temperature is controlled at 30° C.. | / | <0.2% |
| IE6 | / | Four kettle reactors are used and a total residence time in the four kettle reactors is 80 min. | / | <0.2% |
| IE7 | / | Two kettle reactors are used and a total residence time in the two kettle reactors is 50 min. | / | <0.2% |
| CE1 | Aluminum chloride is weighted without nitrogen protection. It is observed that white smoke came out, and aluminum chloride is changed from light yellow to white, indicating that surface of aluminum chloride is deactivated. | / | / | >0.5% |
| CE2 | / | The first reaction temperature is controlled at 5° C.. | / | <0.2% |
| CE3 | / | The second reaction temperature is controlled at 60° C.. | / | <0.2% |
| CE4 | / | Five kettle reactors are used and a total residence time in the five kettle reactors is 90 min. | / | <0.2% |
| CE5 | / | A molar ratio of 2-methylnaphthalene: propionyl chloride: AlCl$_3$ is 1:1.4:1.7. | / | <0.2% |
| CE6 | / | A molar ratio of 2-methylnaphthalene: propionyl chloride: AlCl$_3$ is 1:1.2:1.3. | / | <0.2% |
| CE7 | / | A molar ratio of 2-methylnaphthalene: propionyl chloride: AlCl$_3$ is 1:1.2:1.4. Two materials are injected into the three-way mixer with an inner diameter of 0.5 mm. | / | <0.2% |
| CE8 | / | The raw solution and the acylation liquid are injected into a three-way mixer and introduced in the microchannel reactor for reaction for 65 min, the acylation reaction solution is obtained and flows out. The second reaction temperature is controlled to 35° C.. | / | <0.2% |
| CE9 | / | The acylation reaction liquid flowing out of the kettle reactors is subjected to batch | / | <0.2% |

TABLE 2-continued different conditions of Examples 2-7 and Comparative Examples 1-10

| | Acylation solution preparation | Acylation reaction & hydrolysis | Oil phase distillation | Solid |
|---|---|---|---|---|
| CE10 | / | hydrolysis. The hydrolysate is not introduced to the liquid separator in Example 1. Instead, the oil phase and the water phase are separated by standing for 24 hours. | / | <0.2% |

"/" indicates that the condition in one Example is the same as that in Example 1.

TABLE 3 yield and purity of 2-methyl-6-propionylnaphthalene, and conversion rate and selectivity of 2-methylnaphthalene of Examples 2-7 and Comparative Examples 1-10

| | Conversion (%) | Selectivity (%) | Yield (%) | Purity (%) |
|---|---|---|---|---|
| IE2 | 97.0 | 88.0 | 77.5 | 98.0 |
| IE3 | 99.0 | 88.0 | 80.0 | 98.0 |
| IE4 | 99.0 | 76.5 | 68.5 | 97.0 |
| IE5 | 97.0 | 88.0 | 78.0 | 98.0 |
| IE6 | 99.5 | 88.0 | 80.2 | 98.0 |
| IE7 | 81.6 | 85.0 | 60.5 | 98.0 |
| CE1 | 89.0 | 80.6 | 69.0 | 98.0 |
| CE2 | 99.0 | 80.2 | 78.2 | 98.0 |
| CE3 | 99.5 | 72.5 | 61.5 | 96.0 |
| CE4 | 99.9 | 88.0 | 79.8 | 98.0 |
| CE5 | 99.9 | 88.0 | 80.5 | 98.0 |
| CE6 | 82.0 | 80.0 | 61.0 | 98.0 |
| CE7 | 82.0 | 85.2 | 61.2 | 98.0 |
| CE8 | 99.0 | 85.0 | 76.0 | 98.0 |
| CE9 | 99.0 | 88.0 | 80.0 | 98.0 |
| CE10 | 99.0 | 88.0 | 80.0 | 98.0 |

As shown in Table 2 and Table 3, compared with Example 1, Example 2 does not adopt the suction filtering device for suction filtration to remove all the undissolved solid particles in the acylation liquid. In Example 2, the acylation liquid has the risk of blocking the microchannel reactor 12 in the subsequent operation for the acylation reaction, and the yield of 2-methyl-6-propionylnaphthalene product after the recrystallization is reduced. In addition, the protective atmosphere and control parameters during the preparation of the acylation liquid 15 may affect the preparation and the synthesis. For example, compared with Example 1, in Comparative Example 1, the aluminum chloride is weighted without nitrogen protection, white smoke is observed from the opening of the container, and the color of the aluminum chloride changes from light yellow to white, which indicates that a part of the aluminum chloride at its surface may be deactivated. It can be known that when the AlCl₃ catalyst is contacted with moisture in the air, it is easy to be deactivated, which causes incomplete conversion of 2-methylnaphthalene during the acylation reaction. In addition, it can be seen from the comparison between Example 1 and Comparative Examples 5 to 7 during the acylation reaction that the addition of less propionyl chloride will cause incomplete conversion of 2-methylnaphthalene, and the addition of excess propionyl chloride and catalyst will not further improve the conversion of 2-methylnaphthalene. Therefore, it can be known that the underdoses of propionyl chloride and the inappropriate catalytic temperature will cause incomplete conversion of 2-methylnaphthalene.

Referring to Examples 1 and 4 to 7 in Table 2, influence of different acylation reaction conditions on the acylation reaction process is shown. Compared with IE1, in IE4 to IE and CE2 to CE8, one or more of the following conditions, such as the temperature of the first thermostatic bath where the three-way mixer 11 and the microchannel reactor 12 are placed, the temperature of the second thermostatic bath where the kettle reactors 13 are placed, the number of the kettle reactors 13 in series, the residence time, and the ratio of 2-methylnaphthalene: propionyl chloride: AlCl₃, are changed, it shows that the acylation reaction conditions affect the selectivity of 2-methylnaphthalene and the yield of 2-methyl-6-propionylnaphthalene.

The three-way mixer 11 and the microchannel reactor 12 are placed in the first thermostatic bath for low-temperature mixing, in which the raw material liquid 14 and the acylation liquid 15 are mixed violently exothermically, the heat released from the mixing may be dissipated and transferred to the low temperature side. Moreover, the acylation reaction is under the kinetic control in the low-temperature microreactor area, resulting in fast reaction, and 60% to 70% of 2-methylnaphthalene converted into the acylation products. When the temperature of the kettle reactor 13 is raised, the mixed solution may be reacted in the kettle reactor 13 for a period of time to continue the reaction of unreacted 2-methylnaphthalene, which improves the conversion rate of the reaction, and reduces the cost of using the microchannel reactor 12 in industry. The conversion and the selectivity of the reaction are improved through the accurate control of the temperature of the first and second thermostatic baths. For example, the comparison between Example 1 and Comparative Example 2 in Table 2 shows that changing the temperature of the first thermostatic bath will seriously affect the selectivity of 2-methylnaphthalene. By comparing Example 1 with Comparative Example 3, it can be seen that changing the temperature of the second thermostatic bath will seriously affect the selectivity of 2-methylnaphthalene and the yield of 2-methyl-6-propionylnaphthalene.

Compared with Example 1, in Comparative Example 4, five kettle reactors 13 are used and the total residence time is 90 minutes, which is almost the same as Example 1 except that the experiment time is extended. Compared with Examples 4 to 7, in Comparison Example 8, only the microchannel reactor 12 with an inner diameter of 3 mm is used for the reaction but not combined with the kettle reactors 13, resulting in a low selectivity of 2-methylnaphthalene. The microchannel reactor 12 has high specific surface area, high safety performance, fast temperature response, mainly diffusion mass transfer, and may quickly remove heat from the reaction system and perform reaction on the reactants at an optimal reactant temperature. Although using the microchannel reactor is conducive to improving the selectivity and yield of the reactants, only using the microchannel reactor 12 causes acylation reaction takes a long time, and is not conducive to the later hydrolysis.

In Comparative Example 9, the acylation reaction liquid flowing out of the kettle reactor is hydrolyzed in a batch kettle. Compared with Example 1, in CE9, the acylation reaction liquid flowing out of the kettle reactor 13 is not directly introduced into the tubular reactor for the synchronous hydrolysis, that is, there is a certain time interval between obtaining the acylation reaction liquid and performing the hydrolysis reaction. When water is directly added to the tank for hydrolysis, the acylation reaction liquid cannot be hydrolyzed in time. In addition, when the acylation reaction liquid is stored, it may be hydrolyzed with moisture in the air, and HCl gas will escape, polluting the air. Further, it is difficult for the process in CE9 to control the hydrolysis reaction time, temperature and material balance rate, and the water consumption will be increased by 2 to 3 times. Compared with Example 1, in Comparative Example 10, the acylation reaction liquid and demineralized water flowing out of the kettle reactors are hydrolyzed in the continuous synchronous hydrolysis reactor to terminate the acylation reaction and obtain the hydrolysate, but without the liquid separator in Example 1 to perform the separation. The hydrolysate stands for 24 hours to separate the oil phase and the water phase, which not only requires a longer separation time of at least 24 hours, but also causes waste gas which is generated in the process of liquid separation and pollutes the environment.

In addition, Examples 8 to 12 show acylation wastewater treatment processes of the water phase solution after the separation of the hydrolysate with the liquid separator 16.

Example 8

500 mL of acylation wastewater (COD: 6530 mg/L, nitrobenzene: 3200 mg/L, chloride ion: 3000 mg/L, aluminum ion: 3000 mg/L) is taken into a beaker. 8 g of sodium hydroxide is added, and a pH value is adjusted to 9.0 for reaction for 0.5 h to obtain a suspension containing aluminum hydroxide precipitation. The suspension is filtered to obtain a filter cake and a filtrate, and the filter cake is naturally dried. A pH of the filtrate is adjusted to 2 with 18 wt % hydrochloric acid, and is transferred into a separating funnel filled with 500 mL n-heptane. After shaking, it stands for 30 min to form phase layers. A supernatant (i.e., an extraction phase) is transferred to a rectification column for rectification and recovery at a height corresponding to the 15th plate, with a reflux ratio of 0.06, a top temperature of 98° C., and a bottom temperature of 176° C., so as to obtain nitrobenzene materials with a purity of 99% and an extractant n-heptane with a purity of 98%. A recovery rate of nitrobenzene reaches 90%, and a loss of the extractant n-heptane is only 3%. A lower solution (i.e., a raffinate phase) of the separating funnel is transferred to an activated sludge treatment system for further treatment for 10 h. 10000 mg of dried filter cake is added into a dissolution tank containing 5000 mL of concentrated hydrochloric acid for dissolution at a temperature of 40° C., and react with 500 mg of calcium aluminate at a temperature of 70° C. and a pressure of 0.5 MPa to obtain a product of polyaluminum chloride.

Figure 9:
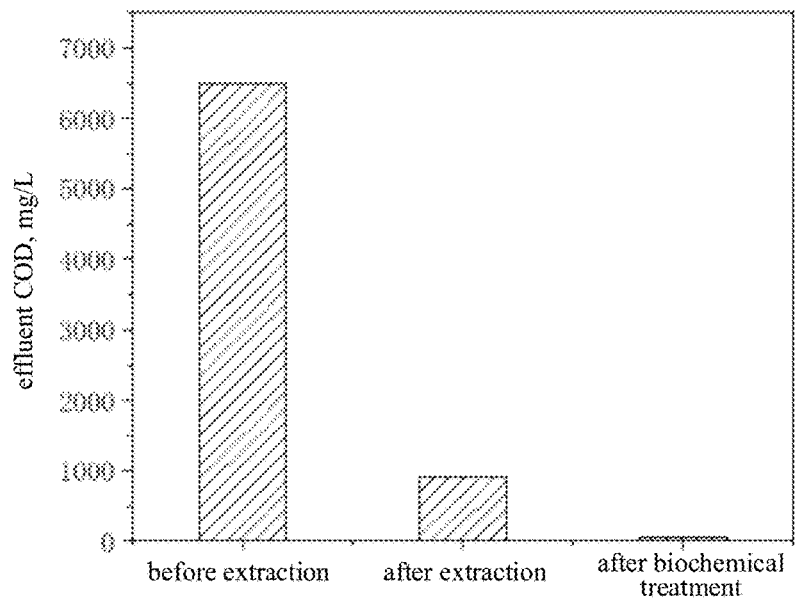
FIG. 9 is a graph showing a change of COD in a water phase separated by a liquid separator with a treatment process in Example 8 of the present disclosure.

After detection, the COD in the effluent after being treated by the activated sludge treatment system is 55 mg/L (as shown in FIG. 9) and the concentration of nitrobenzene is 0.5 mg/L, which meet the requirements of the discharge standard "GB8978-1996 Integrated Wastewater Discharge Standard" (COD<100 mg/L, nitrobenzene<1.0 mg/L). Indicators for the obtained product polyaluminum chloride include a mass fraction of aluminum chloride of 29%, a basicity of 55%, a mass fraction of water insoluble of 0.2, a pH value of 4.5, and a mass fraction of iron of 1.0%. Arsenic, lead, chromium, mercury and cadmium are not detected. All indicators of the product polyaluminum chloride meet the requirements of the standard "GB/T22627-2014 Water Treatment Chemical—Polyaluminium chloride".

Example 9

500 mL of acylation wastewater (COD: 6900 mg/L, nitrobenzene: 2700 mg/L, chloride ion: 3000 mg/L, aluminum ion: 3000 mg/L) is taken into a beaker, 7.5 g of potassium hydroxide is added, and a pH value is adjusted to 9.2 for reaction for 0.5 h to obtain a suspension containing aluminum hydroxide precipitation. The suspension is filtered to obtain a filter cake and a filtrate, and the filter cake is naturally dried. A pH of the filtrate is adjusted to 2.5 with 50 wt % sulphuric acid, and is transferred into a separating funnel filled with 600 mL n-heptane. After shaking, it stands for 30 min to form phase layers. A supernatant (i.e., an extraction phase) is transferred to a rectification column for rectification and recovery at a height corresponding to the 15th plate, with a reflux ratio of 0.06, a top temperature of 98° C., and a bottom temperature of 176° C., so as to obtain nitrobenzene materials with a purity of 99% and an extractant n-heptane with a purity of 98%. A recovery rate of nitrobenzene reaches 92%, and a loss of the extractant n-heptane is only 4%. A lower solution (i.e., a raffinate phase) of the separating funnel is transferred to an activated sludge treatment system for further treatment for 12 h. 10000 mg of dried filter cake is added into a dissolution tank containing 6000 mL of concentrated hydrochloric acid for dissolution at a temperature of 45° C., and react with 400 mg of magnesium aluminate at a temperature of 80° C. and a pressure of 0.7 MPa to obtain a product of polyaluminum chloride.

Figure 10:
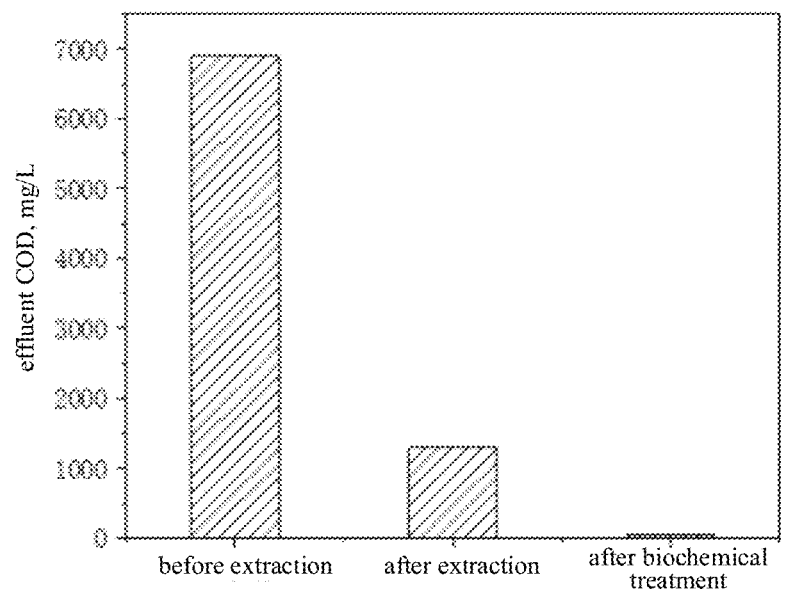
FIG. 10 is a graph showing a change of COD in a water phase separated by a liquid separator with a treatment process in Example 9 of the present disclosure.

After detection, the COD in the effluent after being treated by the activated sludge treatment system is 50 mg/L (as shown in FIG. 10) and the concentration of nitrobenzene is 0.5 mg/L, which meet the requirements of the discharge standard "GB8978-1996 Integrated Wastewater Discharge Standard" (COD<100 mg/L, nitrobenzene<1.0 mg/L). Indicators for the obtained product polyaluminum chloride include a mass fraction of aluminum chloride of 30%, a basicity of 56%, a mass fraction of water insoluble of 0.3, a pH value of 5.0, and a mass fraction of iron of 1.0%. Arsenic, lead, chromium, mercury and cadmium are not detected. All indicators of the product polyaluminum chloride meet the requirements of the standard "GB/T22627-2014 Water Treatment Chemical—Polyaluminium chloride".

Example 10

500 mL of acylation wastewater (COD: 7200 mg/L, nitrobenzene: 4200 mg/L, chloride ion: 3000 mg/L, aluminum ion: 2500 mg/L) is taken into a beaker. 8.2 g of potassium hydroxide is added, and a pH value is adjusted to 9.0 for reaction for 0.5 h to obtain a suspension containing aluminum hydroxide precipitation. The suspension is filtered to obtain a filter cake and a filtrate, and the filter cake is naturally dried. A pH of the filtrate is adjusted to 3 with 15 wt % hydrochloric acid, and is transferred into a separating funnel filled with 600 mL n-heptane. After shaking, it stands for 30 min to form phase layers. A supernatant (i.e., an extraction phase) is transferred to a rectification column for rectification and recovery at a height corresponding to the 15th plate, with a reflux ratio of 0.06, a top temperature of 98° C., and a bottom temperature of 176° C., so as to obtain nitrobenzene materials with a purity of 99% and an extractant n-heptane with a purity of 99%. A recovery rate of nitrobenzene reaches 88%, and a loss of the extractant n-heptane is only 6%. A lower solution (i.e., a raffinate phase) of the separating funnel is transferred to an activated sludge treatment system for further treatment for 12 h. 8000 mg of dried filter cake is added into a dissolution tank containing 5000 mL of concentrated hydrochloric acid for dissolution at a temperature of 50° C., and react with 450 mg of magnesium aluminate at a temperature of 80° C. and a pressure of 0.7 MPa to obtain a product of polyaluminum chloride.

Figure 11:
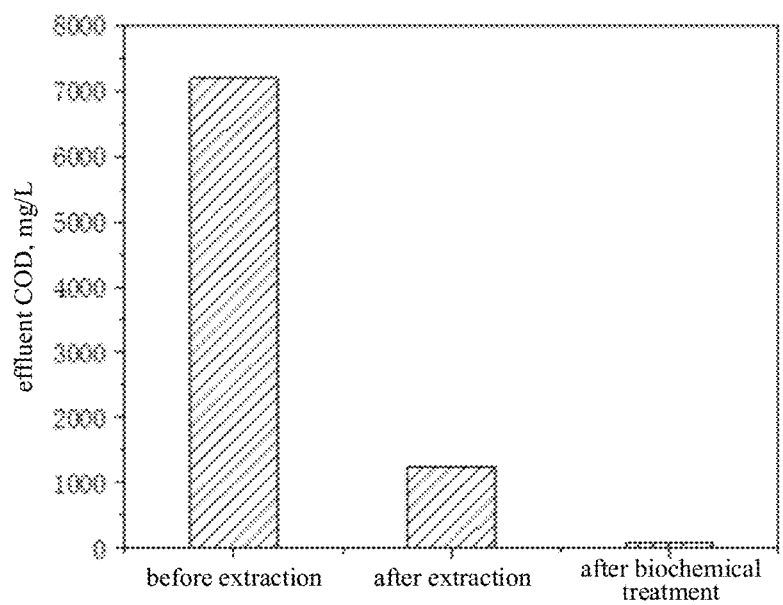
FIG. 11 is a graph showing a change of COD in a water phase separated by a liquid separator with a treatment process in Example 10 of the present disclosure.

After detection, the COD in the effluent after being treated by the activated sludge treatment system is 55 mg/L (as shown in FIG. 11) and the concentration of nitrobenzene is 0.5 mg/L, which meet the requirements of the discharge standard "GB8978-1996 Integrated Wastewater Discharge Standard" (COD<100 mg/L, nitrobenzene<1.0 mg/L). Indicators for the obtained product polyaluminum chloride include a mass fraction of aluminum chloride of 31%, a basicity of 62%, a mass fraction of water insoluble of 0.4, a pH value of 6.5, and amass fraction of iron of 2.0%. Arsenic, lead, chromium, mercury and cadmium are not detected. All indicators of the product polyaluminum chloride meet the requirements of the standard "GB/T22627-2014 Water Treatment Chemical—Polyaluminium chloride".

Example 11

Example 11 is substantially the same as Example 8 except that the extractant is carbon tetrachloride.

Example 12

Example 12 is substantially the same as Example 8 except that the extractant is a mixture of n-octane and xylene in a volume ratio of 1:1.

What is claimed is:

1. A method for continuous synthesis of acylnaphthalene, comprising:
mixing a raw solution containing 2-methylnaphthalene with an acylation liquid to obtain an acylation reaction liquid with a molar ratio of the 2-methylnaphthalene: the acylation agent: the Lewis catalyst of 1:1.3:1.5;
adding the acylation reaction liquid into a microchannel reactor and a plurality of kettle reactors connected in series to perform acylation reaction;
performing hydrolysis reaction on the acylation reaction liquid immediately after the acylation reaction liquid flows out of the plurality of kettle reactors, to obtain a mixed solution; and
subjecting the mixed solution to separation, rectification and crystallization, to obtain 2-methyl-6-propionylnaphthalene.

2. The method according to claim 1, wherein the raw solution and the acylation liquid are injected into a three-way mixer through a syringe for mixing; and
wherein the three-way mixer and the microchannel reactor are placed in a first thermostatic bath at a temperature of −5° C. to 0° C., and the kettle reactor is placed in a second thermostatic bath at a temperature of 30° C. to 50° C.

3. The method according to claim 1, wherein two to four kettle reactors are provided and connected in series with each other, and a total residence time of the acylation reaction liquid in the kettle reactor is in a range of 50 to 80 min.

4. The method according to claim 1, wherein performing the hydrolysis reaction comprises:
introducing water into a water phase pipeline of a hydrolysis section before introducing the acylation reaction liquid obtained after the acylation reaction into the hydrolysis section;
introducing the acylation reaction liquid into an oil phase pipeline of the hydrolysis section after the water flows out of an outlet of the hydrolysis section;
mixing the acylation reaction liquid with the water in a low temperature cold bath to obtain a mixed solution, and introducing the mixed solution into a tubular reactor for the hydrolysis reaction; and
discharging the mixed solution after the hydrolysis reaction through an outlet of the tubular reactor;
wherein during the hydrolysis reaction, the water is kept in a preset flowing state until the mixed solution is completely discharged.

5. The method according to claim 1, wherein subjecting the mixed solution to the separation comprises:
collecting the mixed solution and separating a water phase and an oil phase of the mixed solution by using a liquid separator.

6. The method according to claim 4, wherein the water is introduced into the water phase pipeline of the hydrolysis section at a flow rate of 3 to 15 mL/min through a water injection pump;
wherein a temperature of the low temperature cold bath is in a range of 0° C. to 20° C.; and
wherein a reaction temperature of the tubular reactor is a range of 30° C. to 40° C.

7. The method according to claim 4, further comprising: performing acylation wastewater treatment, the acylation wastewater treatment comprising:
adjusting a pH value of a water phase separated by a liquid separator to alkalinity to obtain a suspension containing an aluminum hydroxide precipitate, and filtering the suspension to obtain an aluminum hydroxide filter cake and a filtrate;
adjusting a pH value of the filtrate to acidity, and adding an extractant to the filtrate, to obtain a raffinate phase and an extraction phase after stirring and standing;
discharging the raffinate phase after being subjected to biochemical treatment;
rectifying and separating the extraction phase to obtain nitrobenzene and the extractant, wherein the nitrobenzene is reused as an organic solvent, and the extractant is reused for the extraction of the filtrate; and
dissolving the filter cake with concentrated hydrochloric acid by heating to obtain a solution, and adding an additive into the solution for polymerization to obtain polyaluminum chloride.

8. The method according to claim 7, wherein adjusting the pH value of the water phase separated by the liquid separator to alkalinity comprises:
adjusting the pH value of the water phase to a range of 8 to 10 with an alkali, and the alkali is selected from sodium hydroxide, potassium hydroxide, liquid ammonia or a combination thereof.

9. The method according to claim 7, wherein adjusting the pH value of the filtrate to acidity comprises:
adjusting the pH value of the filtrate to a range of 2 to 3 with an acid, wherein the acid is selected from hydrochloric acid, nitric acid, sulfuric acid or a combination thereof.

10. The method according to claim 7, wherein the extractant is a non-polar organic solvent, and a volume ratio of the extractant to the filtrate is 0.5:1 to 5:1, and the extractant is selected from n-heptane, n-octane, n-hexane, benzene, toluene, xylene, carbon tetrachloride or a combination thereof.

11. The method according to claim 7, wherein a temperature for dissolving the filter cake is in a range of 40° C. to 50° C., and a weight ratio of the filter cake to concentrated hydrochloric acid is 0.5:1 to 2.5:1.

12. The method according to claim 7, wherein an amount of the additive is in a range of 2 to 10 wt % based on a dry weight of the filter cake, and the additive is selected from calcium aluminate, magnesium aluminate or a combination thereof.

13. The method according to claim 7, wherein the rectifying comprises:
feeding the oil phase into a first rectification column from a middle of the first rectification column for distillation, discharging a first light fraction from a top of the first rectification column and recycling the first light fraction after condensation, and discharging a bottom liquid from a bottom of the first rectification column;
pumping the bottom liquid still hot to a second rectification column for further distillation, discharging a second light fraction from a top of the second rectification column and collecting the second light fraction after condensation, and collecting a product from a side stream of the second rectification column; and
heating a heavy bottom fraction from the second rectification column with a reboiler, and pumping the heavy bottom fraction still hot to a bottom collection tank.

14. The method according to claim 13, wherein the first rectification column has a pressure in a range of 0.05 KPa to 10 KPa and a reflux ratio in a range of 1:1 to 2:1; and
wherein a condensation temperature of the first rectification column is in a range of 10° C. to 20° C.

15. The method according to claim 13, wherein the second rectification column has a pressure in a range of 0.05 KPa to 10 KP and a reflux ratio in a range of 5:1 to 10:1; and
wherein a condensation temperature of the second rectification column is in a range of 50° C. to 90° C.

16. The method according to claim 1, wherein the 2-methylnaphthalene has a purity of 99.0 to 99.9%, and is extracted from a wash oil by:
performing distillation and separation on the wash oil to obtain a methylnaphthalene-enriched fraction;
introducing the methylnaphthalene-enriched fraction into an azeotropic rectification column for azeotropic distillation to obtain an azeotropic distillate;
introducing the azeotropic distillate into a separator to obtain crude 2-methylnaphthalene; and
introducing the crude 2-methylnaphthalene into a plurality of batch melting crystallizers arranged in parallel for crystallization and purification to obtain the 2-methylnaphthalene.

17. The method according to claim 1, wherein the acylation liquid is prepared by:
weighing a Lewis catalyst under inert gas protection;
adding a solvent and the Lewis catalyst into a first chamber through a first feeding port and mixing them with an agitator to obtain a mixture solution; and
adding an acylation agent into the mixture solution with a feeding pump to obtain the acylation liquid;
wherein a molar mass ratio of the acylation agent to the Lewis catalyst is (1.1 to 1.5):(1.3 to 1.7); and/or a molar mass ratio of the Lewis catalyst to the solvent is 1.3:5 to 1.7:5.

18. The method according to claim 17, wherein the solvent is nitrobenzene, and adding the nitrobenzene and the Lewis catalyst into the first chamber and mixing them comprises:
adding the nitrobenzene into the first chamber through the first feeding port;
adding the Lewis catalyst to the nitrobenzene in the first chamber; and
heating the nitrobenzene and the Lewis catalyst to 50° C. to 60° C. by using the heat exchange medium under stirring at a stirring speed of 200 rpm to 400 rpm with the agitator.

19. The method according to claim 17, wherein preparing the acylation liquid further comprises:
filtering the acylation liquid in an inert gas atmosphere with a suction filtering device to obtain a filtered acylation liquid.

20. The method according to claim 17, wherein the acylation agent is added at a speed of 3 drops to 10 drops per second, and a stirring speed of the agitator is 200 rpm to 400 rpm.

* * * * *